United States Patent [19]

Hoffmann et al.

[11] Patent Number: 5,150,292
[45] Date of Patent: Sep. 22, 1992

[54] METHOD AND SYSTEM FOR DETERMINATION OF INSTANTANEOUS AND AVERAGE BLOOD FLOW RATES FROM DIGITAL ANGIOGRAMS

[75] Inventors: Kenneth R. Hoffmann, Chicago; Kunio Doi, Hinsdale, both of Ill.

[73] Assignee: Arch Development Corporation, Chicago, Ill.

[21] Appl. No.: 428,059

[22] Filed: Oct. 27, 1989

[51] Int. Cl.⁵ ............................................. G06F 15/00
[52] U.S. Cl. ............................... 364/413.07; 250/303; 128/654; 128/691
[58] Field of Search ............ 128/653 R, 653 AF, 654, 128/691; 250/303; 364/413.07, 413.23; 378/62

[56] References Cited

U.S. PATENT DOCUMENTS

| | | | |
|---|---|---|---|
| 3,824,399 | 7/1974 | Björk et al. | 378/62 |
| 4,103,679 | 8/1978 | Aronson | 364/413.07 |
| 4,263,916 | 4/1981 | Brooks et al. | 128/654 |
| 4,692,864 | 9/1987 | Shimoni et al. | 364/413.23 |
| 5,048,534 | 9/1991 | Marinus et al. | 128/713 |

OTHER PUBLICATIONS

Hoffmann et al. "Automated tracking of the vascular tree in DSA images using a double-squate-box region-of-search algorithm" SPIE vol. 626 Medicine XIV/PACS IV, pp. 326–333 (1986).
Fujita et al. "Image feature analysis and computer-aided diagnosis in digital radiography" Med. Phys. 14(4), Jul./Aug. 1987 pp 549–556.

Primary Examiner—Dale M. Shaw
Assistant Examiner—Laura Brutman
Attorney, Agent, or Firm—Oblon, Spivak, McClelland, Maier & Neustadt

[57] ABSTRACT

A method and system for quantitation of blood flow rates by using digital subtraction angiographic (DSA) images, wherein the spatial shift of the distribution of contrast material injected into an opacified vessel in the acquired angiographic images is analyzed as a bolus of the contrast material proceeds through the vessel. In order to determine the distance that the bolus travels between image acquisitions, there is obtained from the DSA images the distribution of vessel contrast along the length of the vessel, called and "distance-density" curve. The distance that the contrast material travels during the time between two images acquisitions is determined by means of cross correlation of the two respective distance-density curves. The flow rate between the image acquisitions is calculated by multiplying this distance by the frame rate and the vessel cross-sectional area which is estimated from the vessel size assuming a circular cross section. Thus, for high frame-rate acquistions, instantaneous blood flow rates can be determined. The method and system are particularly useful for measurement of pulsatile blood flow rates.

24 Claims, 23 Drawing Sheets

METHOD AND SYSTEM FOR DETERMINATION OF INSTANTANEOUS AND AVERAGE BLOOD FLOW RATES FROM DIGITAL ANGIOGRAMS

The present invention was made in part with U.S. Government support under grant number 2 R01 CA24806-11 and grant number 5 R01 CA47043-03 from the Department of Health and Human Services and the National Cancer Institute. The U.S. Government has certain rights in the invention.

BACKGROUND OF THE INVENTION

1. Field of the Invention

This invention relates generally to blood flow measurement, and more particularly to a method and system for measuring instantaneous and average blood flow rates from digital angiograms.

2. Background of the Invention

Vascular disease is a major cause of death in the U.S. Each year, approximately 500,000 Americans die of sudden cardiac death alone, and the pathologic findings almost invariably implicate coronary atherosclerosis. Vascular disease is also associated with stroke, brain ischemia, hypertension, and loss of limb because of poor perfusion. However, many of these effects may be reversible or preventable if vascular disease is diagnosed early. Thus, detection of vascular abnormalities, such as stenosis (i.e., regions in which the vessel diameter is narrower due to plaque in the vessel), and evaluation of their severity could improve patient prognosis.

In angiography, a sequence of two-dimensional images of the vascular system (angiograms) are acquired by the projection of X-rays through blood vessels into which a bolus of a contrast material is being injected. The appearance of the blood vessels may be further enhanced by the subtraction of a pre-injection image from a post-injection image, so that the background anatomic structures are eliminated. In clinical practice, the severity of vascular disease is usually assessed by visual interpretation of angiograms. This subjective assessment of severity is, by its nature, inaccurate. Indeed, several studies have documented that there is a large intra- and inter-observer variability in the subjective visual examination of stenosis. To reduce the uncertainty of subjective evaluation of vessel diameters, computerized methods have been developed for quantitative analysis of angiograms. (See B. G. Brown, et al.: "Quantitative Coronary Arteriography: Estimation of Dimensions, Hemodynamic Resistance, and Atheroma Mass of Coronary Arteriograms", Circulation 55:231 (1974); J. H. C. Reiber, et al.: "Coronary Artery Dimensions From Cineangiograms: Methodology and Validation of a Computer-assisted Analysis Procedure", IEEE Trans Med Imaging MI-3:131 (1984); M. A. Simons, et al.: "Vessel Diameter Measurement Using Digital Subtraction Radiography", Invest Radiol 20:510 (1985); M. T. LeFree et al.: "Digital Radiographic Assessment of Coronary Arterial Geometric Diameter and Videodensitometric Cross-sectional Area", SPIE 626:335 (1986); E. L. Nickoloff, et al.: "Evaluation of a Cinevideodensitometric Method for Measuring Vessel Dimensions From Digitized Angiograms", Invest Radiol 22:875 (1987); H. Fujita, et al.: "Image Feature Analysis and Computer-aided Diagnosis in Digital Radiography. 2. Computerized Determination of Vessel Sizes in Digital Subtraction Angiography", Med Phys 14:549 (1987); and L. E. Fencil, et al.: "Accurate Analysis of Blood Vessel Sizes and Stenotic Lesions Using Stereoscopic DSA System", Invest Radiol 23:33 (1988).) However, neither absolute vessel size nor percent stenosis directly reveals the functional significance of stenosis, i.e., the hemodynamic effect on blood flow.

The relationship between the degree of stenosis and the functional significance of stenotic regions in coronary arteries has been investigated by Gould et al.: "Experimental Validation of Quantitative Coronary Arteriography for Determining Pressure-flow Characteristics of Coronary Stenosis", Circulation 66:930 (1982), who found that classical fluid-dynamics equations were applicable to tapering stenoses in flexible coronary arteries in vivo. Although this implies that the pressure-flow relationship that characterizes the severity of stenosis can be predicted from the degree of stenosis, the determination of the functional significance still requires the measurement of actual pressure gradients across the stenotic region or the measurement of blood flow rates, i.e., the volume of blood flowing through the vessel per unit time. Because measurement of pressure gradients requires the insertion of a pressure probe near the stenotic region (a difficult clinical procedure), methods to determine blood flow rates have been studied by many investigators as described in detail below. It should be noted that blood flow rates can be measured by using an electromagnetic flow probe. However, this method also requires the placement of a sensor near the stenosis, and is considered undesirable in clinical practice due to the invasive aspect of this procedure.

Blood flow rates, can be calculated using the cross-sectional area of the vessel and the velocity of blood, as shown in FIG. 1. The accuracy of the calculated flow rates will depend on the accuracy of the estimation of the cross-sectional area as well as the accuracy of the velocity measurements. Therefore, blood flow rates determined from angiograms are expected to be more accurate than those estimated using magnetic resonance or ultrasound techniques because of the high spatial resolution of angiographic images.

In angiography, images are acquired as a temporal sequence while a bolus of contrast material proceeds through a vessel. The image contrast of an opacified vessel at any particular location usually changes from one image to the next, i.e., the image contrast of the vessel is a function of time. For analysis by the computer, the angiograms are digitized by converting the optical density in each area (pixel) of the image to numerical values (pixel values). The vessel contrast is defined here as the difference between the pixel value at the center of opacified vessel and the pixel value in the adjacent background. The vessel contrast is related to the concentration of the contrast material in the vessel. FIG. 2 illustrates the change of the vessel contrast as a function of time. This curve (or any similar curve in which other quantities related to vessel contrast, such as concentration and film density, is plotted) is often referred to as a time-density curve. Note that in this curve the vessel contrast increases as the contrast bolus arrives and then decreases as the bolus proceeds farther along the vessel.

A number of investigators have attempted to measure blood flow rates from angiograms (see F. K. Schmiel, et al.: "Densitometric Measurements of Coronary Blood Flow. Methodological Improvement", *Roentgen Video Techniques for Dynamic Studies of Structure and Function of the Heart and Circulation*, P. H. Heintzen and J.

H. B. Buersch (eds). Georg Thieme Publishers (Stuttgart: 1978), pg. 49; P. Spiller, et al.: "Measurements of Systolic and Diastolic Flow Rates in the Coronary Artery System by X-ray Densitometry", Circulation 68:337 (1983); G. Forbes, et al.: "Phantom Testing of Peripheral Artery: Absolute Blood Flow Measurement With Digital Arteriography", Invest Radiol 20:186 (1985); D. L. Parker, et al.: "Flow Measurements From 3D Reconstruction of Moving Arterial Beds From Digital Subtraction Angiography", Computers in Cardiology, IEEE Computer Society 817:281 (1986); D. K. Swanson, et al.: "Arterial Blood-flow Waveform Measurement in Intact Animals: New Digital Radiographic Technique", Radiology 161:323 (1986); and L. E. Fencil, et al.: "Measurements of Absolute Flow Rate in Vessels Using a Stereoscopic DSA System", Phys Med Biol 34:659 (1989)). Vessel cross-sectional areas were estimated from the measured vessel size by assuming a circular cross section for the vessel. Vessel sizes in the images were determined either from the full width at half maximum of the vessel profile or from densitometric methods. Magnification factors and lengths of vessel segments were estimated by placement of calibration rods, balls, or grids near the vessel of interest, or by using the biplane imaging technique.

Most of these investigators determined velocity of the bolus by estimating the amount of time (the time of transmit) required for the bolus to traverse the 1 distance between two locations in the vessel. The time of transit is usually estimated from time parameters calculated from the time-density curves which were obtained at specified locations in the vessel. It should be noted that a number of time parameters may be determined from these curves, namely, the time that the bolus arrives (Ta), the time that the vessel contrast reaches one-half its maximum value (Thp), the time that the vessel contrast reaches its maximum or peak value (Tp), and the mean transit time (MTT) of the bolus, which is obtained from the first moment of the time-density curve. For steady-flow conditions, accurate flow rates have been calculated using Tp and MTT. However, for pulsatile-flow conditions, such as in arterial flow, the flow rates calculated using MTT and Tp have been found to vary by as much as one-hundred percent of the average flow rates, and the average error in the calculated flow rates is approximately twenty percent.

FIGS. 3a and 3b show comparisons of flow rates obtained by using MTT ant Tp, respectively (circles), and those measured by an electromagnetic flow meter (lines). The solid line indicates the average flow rates, and the dashed lines indicate the minimum and maximum flow rates as measured by the electromagnetic flow meter. It is apparent that the measured flow rates obtained from the analysis of the time-density curves fluctuate considerably about the line indicating the average flow rate and lie between the minimum and maximum flow rates measured by the electromagnetic flow meter.

These results may be understood by considering a pulsatile flow pattern, as represented in FIG. 4, as measured by the electromagnetic flow meter. During the pulse cycle of approximately one second, the flow rate peaks sharply for the period of approximately one-fourth second and is relatively low for the rest of the cycle. It should be noted that the flow rate obtained by analysis of time-density curves is approximately the average flow rate during the time of transit. Thus, for pulsatile flow conditions, the flow rate obtained from analysis of time-density curves will depend on the portion of the pulse cycle over which the time of transit occurs, and consequently the measured flow rates will fluctuate between the minimum and maximum flow rates.

Another important factor which probably contributes to the observed inaccuracies in measured flow rates is the change in the shape of the time-density curves due to the pulsatile nature of the flow. This was observed (see J. H. Buersch: "Use of Digitized Functional Angiography to Evaluate Arterial Blood Flow", Cardiovasc Intervent Radiol 6:303 (1983)) in data obtained from a pig aorta and also in vessel phantom studies performed by the present inventors. FIG. 5 shows the time-density curves obtained at locations spaced uniformly along the vessel. Although the overall trends appear similar, it is obvious that the shapes of the curves are considerably different. Therefore, the time parameters determined from these curves are expected to be poorly correlated. Thus, the calculated flow rates will be unreliable.

These results indicate that techniques which employ time-density curves cannot provide reliable estimates of flow rates under pulsatile conditions. Thus, these techniques will probably not be useful in the clinical setting.

Rather than analyzing time-density curves, Swanson et al., supra, attempted to determine the distance that a bolus of contrast material moves between two acquisitions by comparing the total radiographic densities in regions of interest (ROIs) in images of arteries. Note that the radiographic density is related to the vessel contrast. Note also that the total radiographic densities in the two ROIs will not be equal in general because contrast material flows into and out of the ROIs as the blood flows through the vessel. When the total radiographic densities are not equal, the position of the ROI in the second image is shifted iteratively until its total radiographic density is equal to that of the ROI in the first image. The distance that the second ROI is shifted is considered to be the distance that the bolus traversed between the two acquisitions. The flow rate of the bolus is then determined using this distance, the frame rate (or time interval between image acquisitions), and the cross-sectional area of the vessel which is estimated from the measured vessel size using a circular cross-section model. The peak and mean flow rates presented in their studies indicate a 20–25% error in the estimation of flow rates. This may be partly due to inaccuracy in the geometrical measurements such as magnification and vessel cross-sectional area. Additional factors could be the implicit assumptions that contrast material uniformly fills the vessel and that the X-ray beam quality remained constant during the acquisitions. In addition, the orientation of the vessel axis relative to the X-ray beam and the position of the vessel in the image are assumed to remain constant. Thus, this technique would not be applicable to curved or moving vessel segments.

Parker et al., supra, determined the velocity of the bolus using the distance that the leading edge of the bolus traversed between frames. Their calculated flow rates were consistently 18% higher than the flow rates determined using an electromagnetic flow meter. This overestimation may be due to diffusion effects at the front edge of the bolus. An additional source of error could be attributed to the effects of laminar flow. In the case of laminar flow, the velocity of the fluid at the center of the vessel is twice the average velocity in the vessel. It should be noted that for angiographic techniques, the flow rate measured is that of the region occupied by the contrast material. The contrast material of the leading edge of the bolus tends to be located in the center of the vessel. Thus, methods which use only the leading edge to measure flow rates will probably always overestimate flow rates.

The digital images used in the phantom study by Fencil et al., Phys. Med. Biol. 34:659 (1989), supra, were obtained with a Digitron 2 DSA system (Siemens Gammasonics, Des Plaines, Ill.). All images were acquired with a matrix size of 512×512 and a pixel size of 0.36 mm. The image data from the Digitron 2 were analyzed with a VAX 11/750 computer (Digital Equipment Corporation, Maynard, Mass.) connected to a Gould-DeAnza FD5000 image processor and CRT display. The vessel phantom consisted of non-distensible tygon tubing with a 6.7 mm nominal inner diameter. The phantom was imaged with a 9 cm thick lucite plate which provides scatter. A pulsatile pump (Harvard Apparatus, South Natick, Mass.) was used for supply of 0.9% normal saline solution through the phantom. Instantaneous as well as average flow rates were measured with a 6.7 mm extracorporeal flow probe and a Cliniflow electromagnetic flowmeter equipped with a strip chart recorder (Carolina Medical Electrons, King, N.C.). The pulsatile frequency of the pump was maintained at 1 Hz, and experiments were performed for average flow rates ranging from 200 to 650 cc/min. Up to 58 images were acquired at 15 frames/sec, as an injection of 2 cc of Renographin was delivered with an Angiomat 3000 injector (Liebel-Flarsheim, Cincinnati, Ohio) over 0.25 to 0.5 sec.

SUMMARY OF THE INVENTION

Accordingly, one object of this invention is to provide a novel method and system which provides accurate, reliable and reproducible measurement of blood flow rates.

Another object is to provide a novel method and system for accurate, reliable and reproducible measuring of average and instantaneous blood flow rates under pulsatile flow conditions.

Another object of this invention is to provide a novel method and system which permit accurate measurement of blood flow rates and which is useful for evaluation of the functional significance of vascular disease and of the effect of treatment.

These and other objects are achieved according to the present invention by providing a new and improved method and system for quantization of blood flow rates by analyzing the spatial shift of the distribution of the contrast material in the opacified vessel in the DSA images acquired as a bolus of the contrast material proceeds through the vessel. This approach is useful, since conventional methods, in which the time shift of the distribution (based on the so-called "time-density" curves) is analyzed, do not provide reliable results for pulsatile flow.

In order to determine the distance that the bolus travels between image acquisitions, according to the present invention, there is obtained from the images the distribution of vessel image contrast along the length of the vessel, which is hereinafter called the "distance-density" curve. The distance that the contrast material travels during the time between the two image acquisitions is determined by means of cross correlation of the two respective distance-density curves. The flow rate between the image acquisitions is calculated by multiplying this distance by the frame rate and the vessel cross-sectional area which is estimated from the vessel size assuming a circular cross section. Thus, for high frame-rate acquisitions, "instantaneous" blood flow rates can be determined. For angiograms obtained at 15 frames/sec, the instantaneous flow rates measured based on the teachings of the present invention agreed with those measured with an electromagnetic method to within an average of 2 cc/sec for pulsatile flow conditions with peak flow rates of up to 20 cc/sec, and flow rates averaged over the pulse cycle agreed to within 10%.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 6:
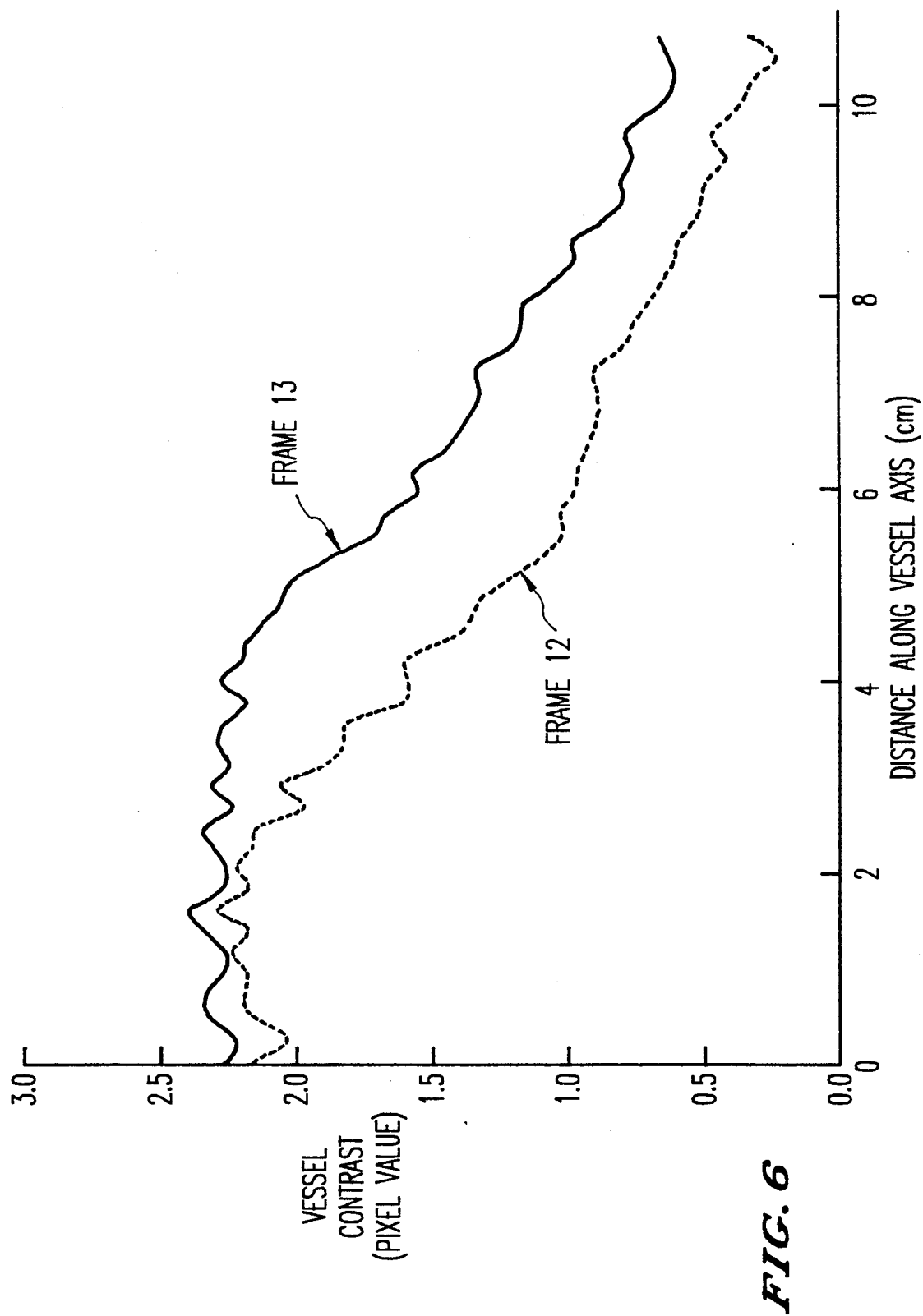
FIG. 6 is a graph illustrating distance-density curves obtained from the 12th and 13th frames.
Figure 7:
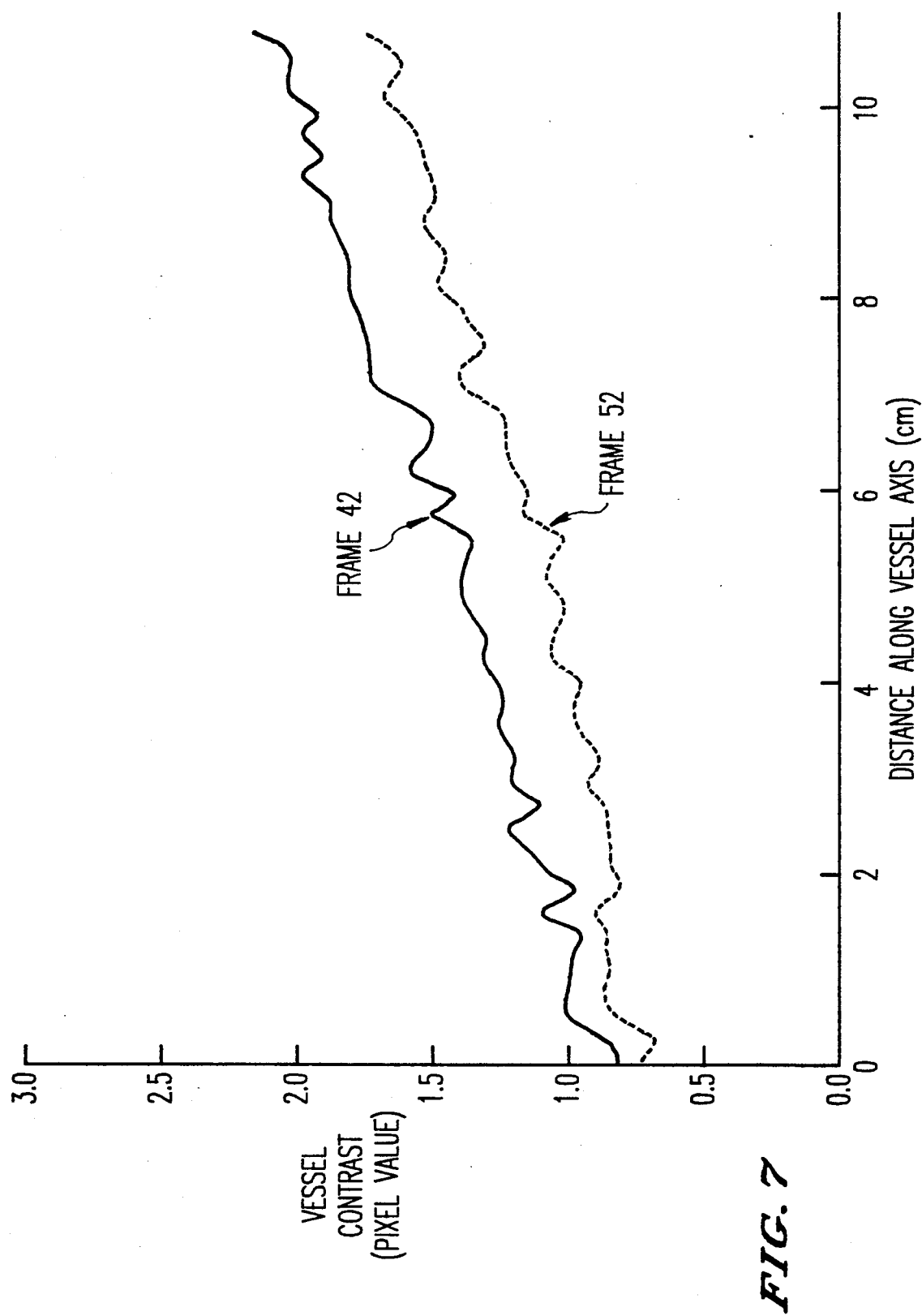
FIG. 7 is a graph illustrating distance-density curves obtained from the 42nd and 52nd frames.

Referring now to the drawings, there is next described the method of the present invention for determining accurate instantaneous blood flow rates from digital angiograms for both steady- and pulsatile-flow conditions. In this method, the spatial distribution of the contrast bolus along the length of the vessel in the angiograms is analyzed. For simplicity, this distribution is called the "distance-density" curve. Examples of the distance-density curves obtained from images acquired during the arrival of the bolus (frames 12 and 13) are shown in FIG. 6. Note that the shapes of the two curves appear to be very similar for vessel contrasts in the range from 0.7 to 1.7 pixel values. The shapes of the distance-density curves obtained during the washout phase (e.g., frames 42 and 52) are also very similar, as is seen in FIG. 7. These comparisons indicate that the shape of the distance-density curves remains fairly constant over short time intervals as the bolus proceeds along the vessel. Thus, the distance that the bolus moves along the vessel between two image acquisitions can be determined by comparing the distance-density curves obtained from the acquired angiograms. The flow rates between acquisitions can be obtained by multiplying this distance by the frame rate and the cross-sectional area of the vessel.

Figure 8:
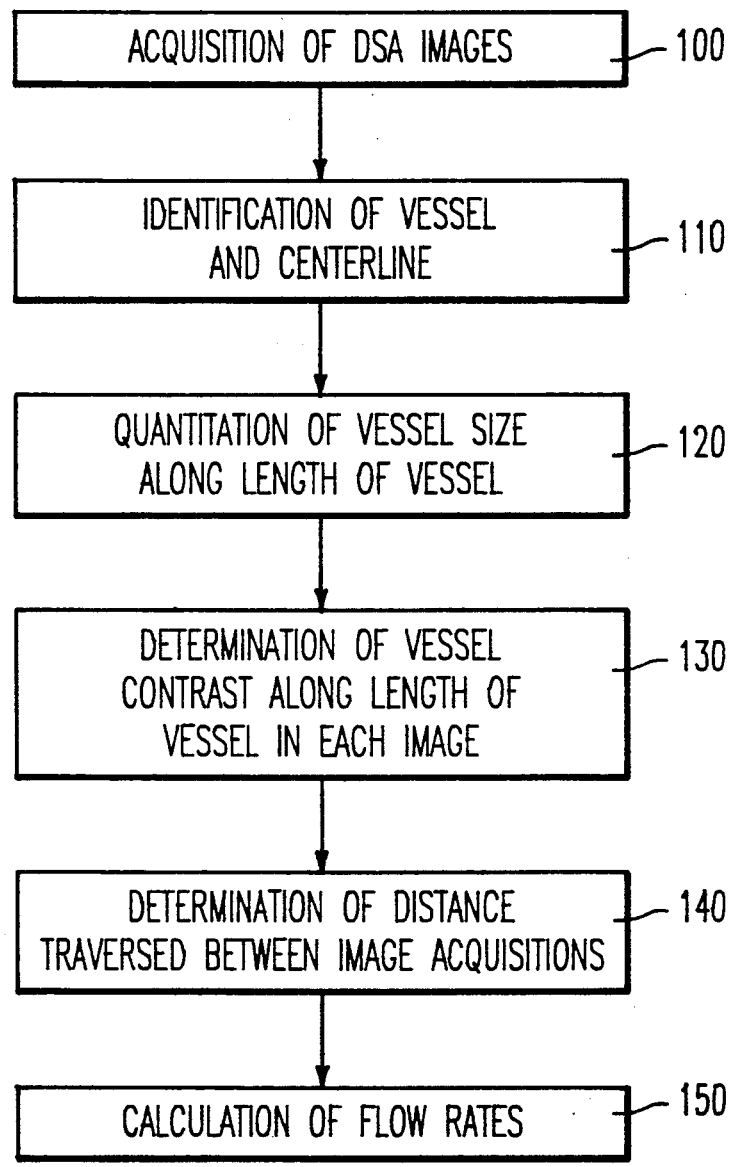
FIG. 8 is a flow chart illustrating steps performed in the determination of blood flow rates from digital angiograms.

FIG. 8 illustrates the overall scheme of the present invention for the determination of blood flow rates from angiograms. First, DSA images are acquired (step 100). Then, a vessel or vessel region is selected for analysis, and the vessel centerline is determined in each image (step 110). From the vessel size, which is quantified along the length of the vessel, the cross-sectional area is estimated assuming a circular cross section for the vessel (step 120). The vessel contrast is then determined as a function of distance along the vessel centerline for each angiogram (step 130). The distance that the bolus traversed between two image acquisitions is determined by cross-correlation of the distance-density curves obtained from the two images (step 140). The "average" flow rate during the acquisitions is then calculated from this distance, the time between acquisitions, and the cross-sectional area of the vessel (step 150). Thus, for high frame rate acquisitions, "instantaneous" blood flow rates can be determined.

Figure 9:
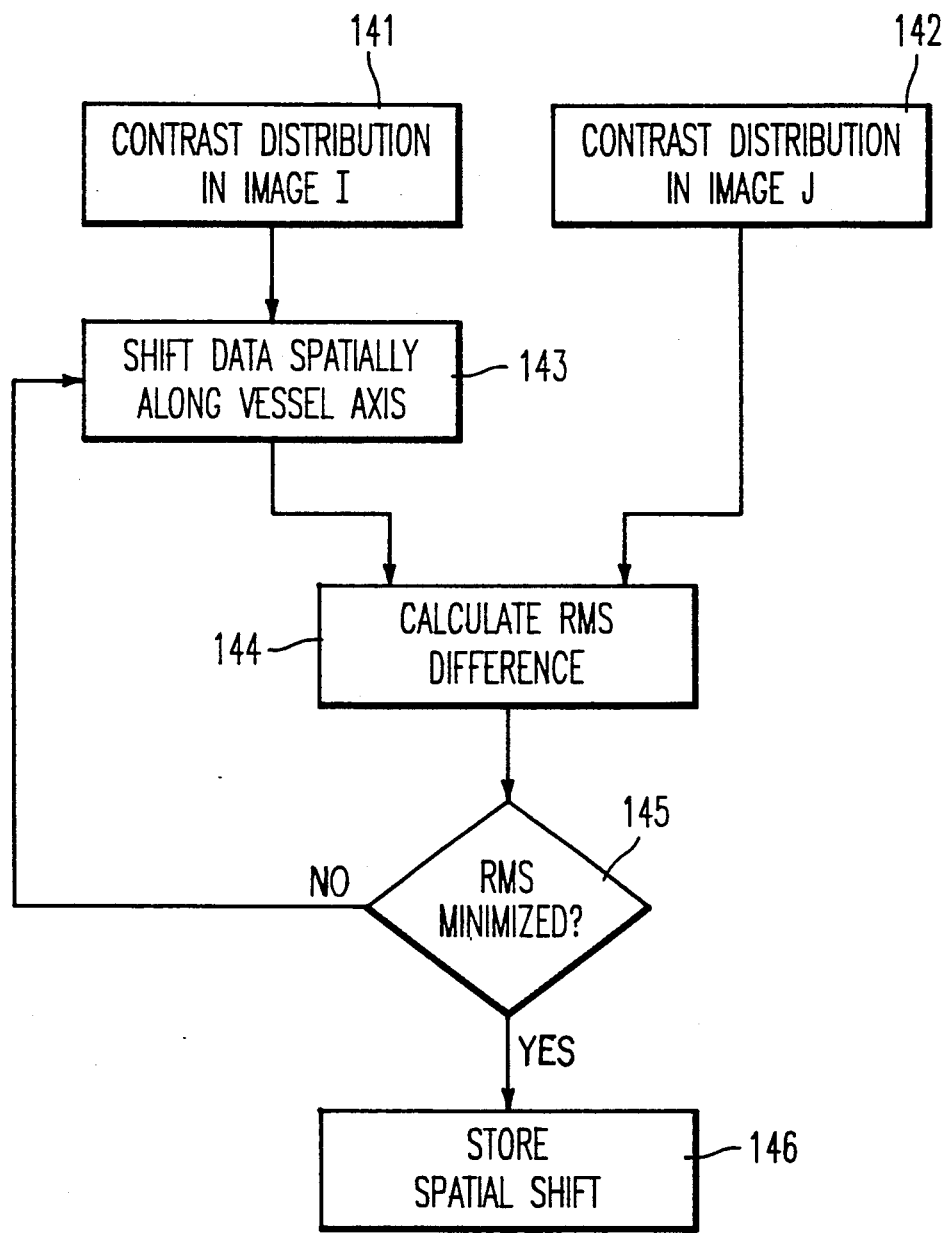
FIG. 9 is a flow chart illustrating steps performed in the determination of the distance (spatial shift) that the contrast material traversed between image acquisitions.

A schematic flow chart of the method of the present invention for determination of the distance traversed by the bolus between the acquisition of two images is shown in FIG. 9. The distance-density curve is obtained from one image (step 141) and from another image (step 142). The two distance-density curves are then compared by calculating the root-mean-square (RMS) difference between the two curves (step 144). The RMS difference is calculated for the vessel regions in which the vessel contrast values of the curves overlap. It should be noted that the images may be separated by more than one acquisition interval, i.e , "I" need not be equal to "J+1". One of the curves is shifted spatially (step 143) in an iterative manner until the RMS difference is minimized as determined in step 145. The spatial shift which yields the minimum RMS difference is considered as the distance that the bolus traversed between the two acquisitions and is stored in memory at step 146.

In order to improve statistical accuracy and to maintain flexibility for further analysis, the distances traversed between the image acquisitions are summed beginning with the first image frame. Thereby, the cumulative distance (and subsequently the cumulative vessel volume calculated by multiplying the distance by the vessel cross-sectional area) is obtained as a function of time. The "instantaneous" slope of the curve representing the relationship between the cumulative volume and time (FIG. 10) is equal to the "instantaneous" flow rate.

Next described are results obtained by mean of the method of the present invention.

The images acquired in the phantom study by Fencil et al, described above, were analyzed using the present method for determination of blood flow rates. The vessel diameter was 6.7 mm (approximately 19 pixels in the image). The vessel was assumed to have a circular cross section. The vessel axis was oriented parallel to the imaging plane. The length of the vessel segment employed from this study was 10.8 cm. The distance-density curves were obtained by averaging the pixel values within small regions of interest, 5×5 pixel area, centered in the vessel and spaced at 7 pixel intervals. The distances in the vessel were corrected for magnification.

Figure 1:
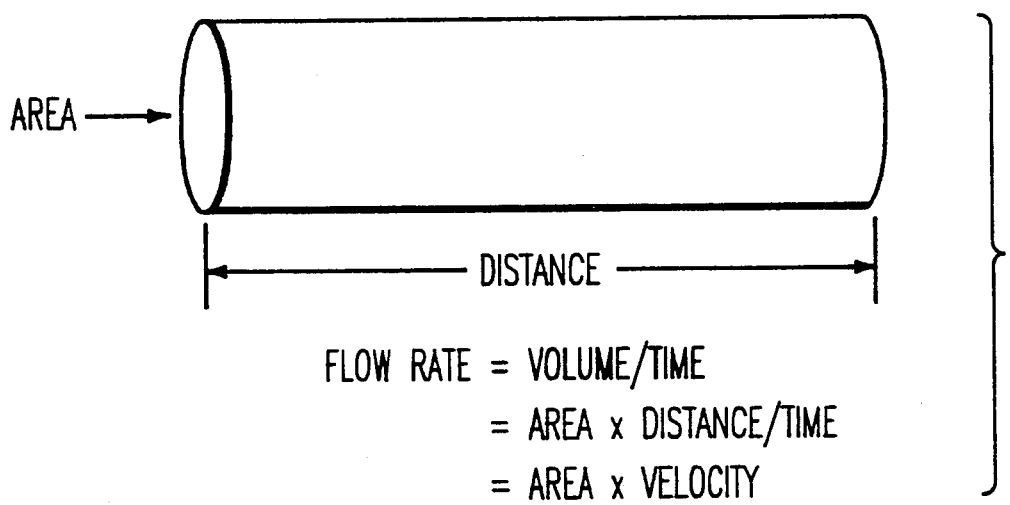
FIG. 1 is a diagram illustrating the basic relationship flow rate with volume, area, distance, velocity, and time.
Figure 2:
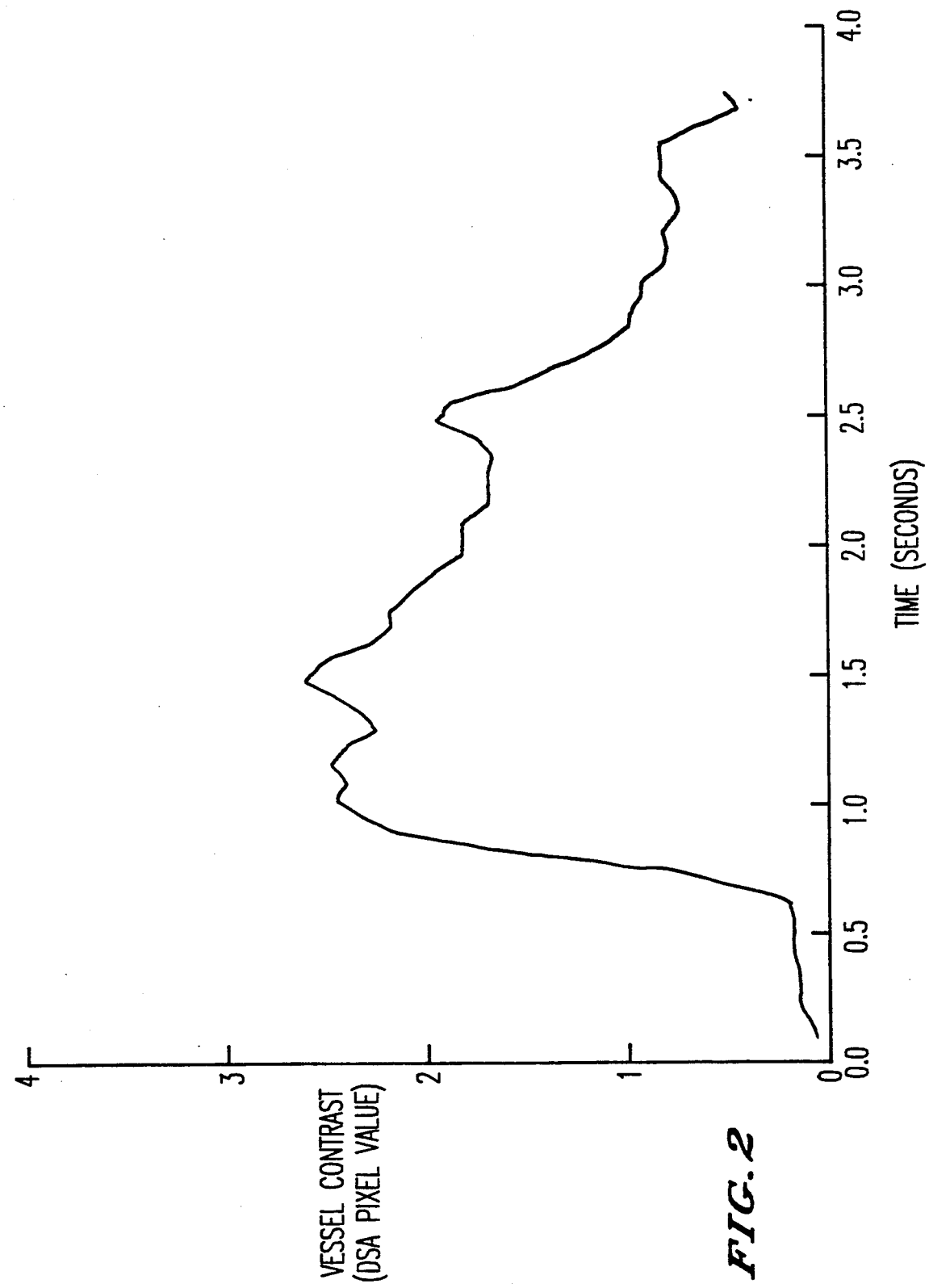
FIG. 2 is a time-density curve illustrating the flow of a bolus past a selected location in a vessel.
Figure 3A:
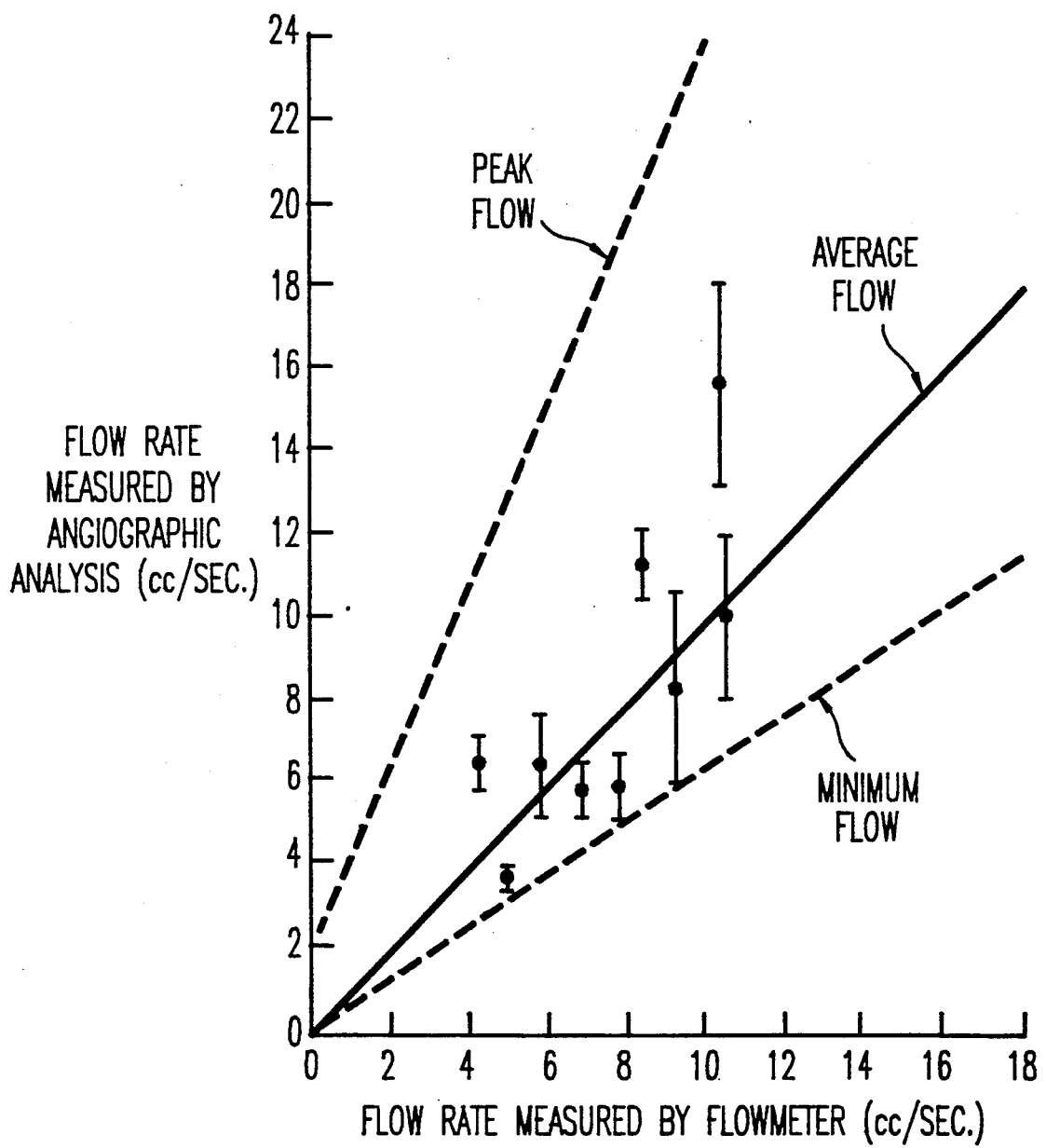
FIGS. 3a and 3b are graphs illustrating results of flow rate measurements using MTT and Tp obtained from time-density curves, respectively, indicating large variations in the measured flow rates.
Figure 3B:
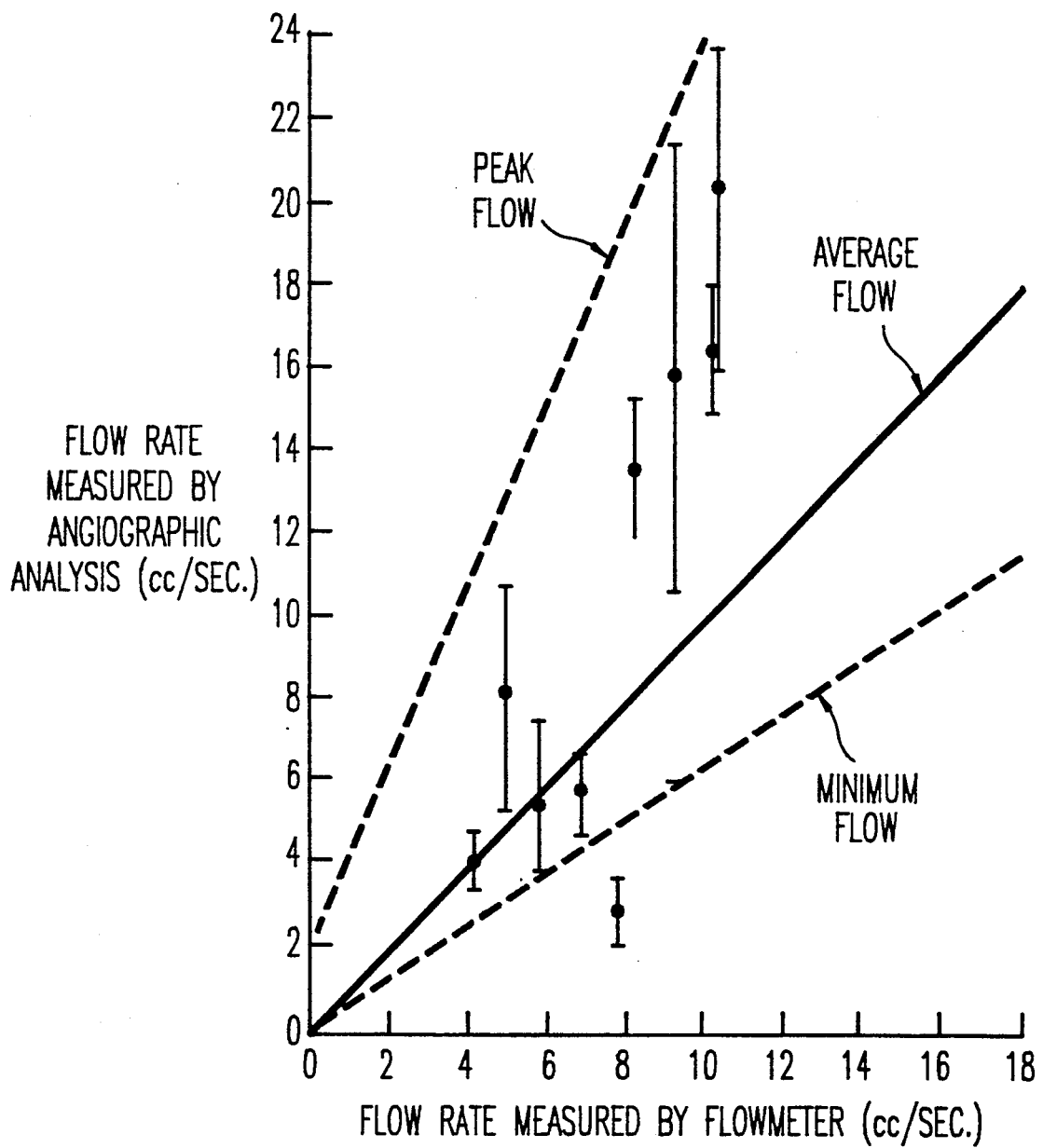
Figure 4:
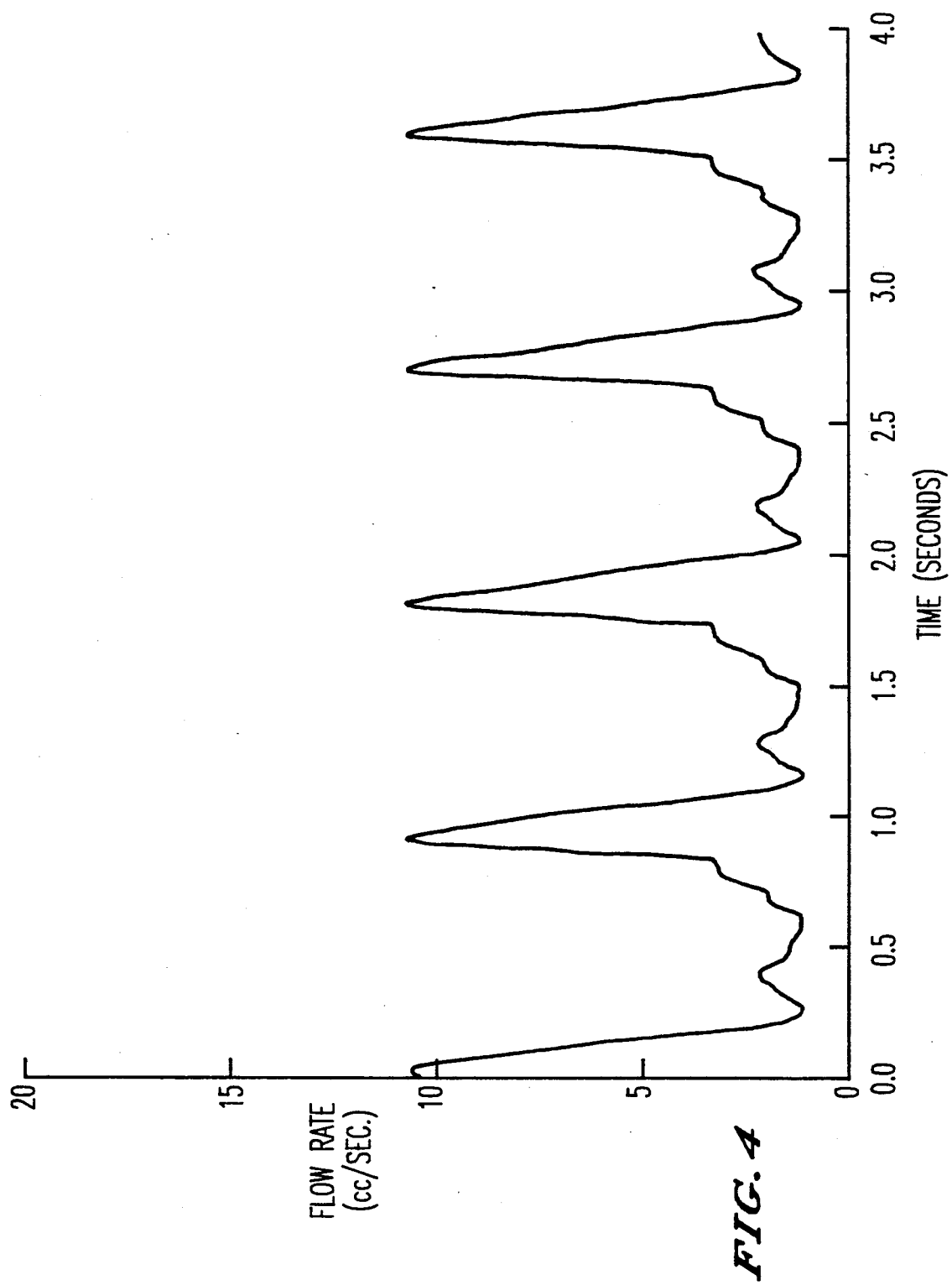
FIG. 4 is a graph of flow rate as a function of time measured by an electromagnetic flow meter for pulsatile flow conditions, wherein the flow rate averaged over one pulse cycle is 3.5 cc/sec.
Figure 5:
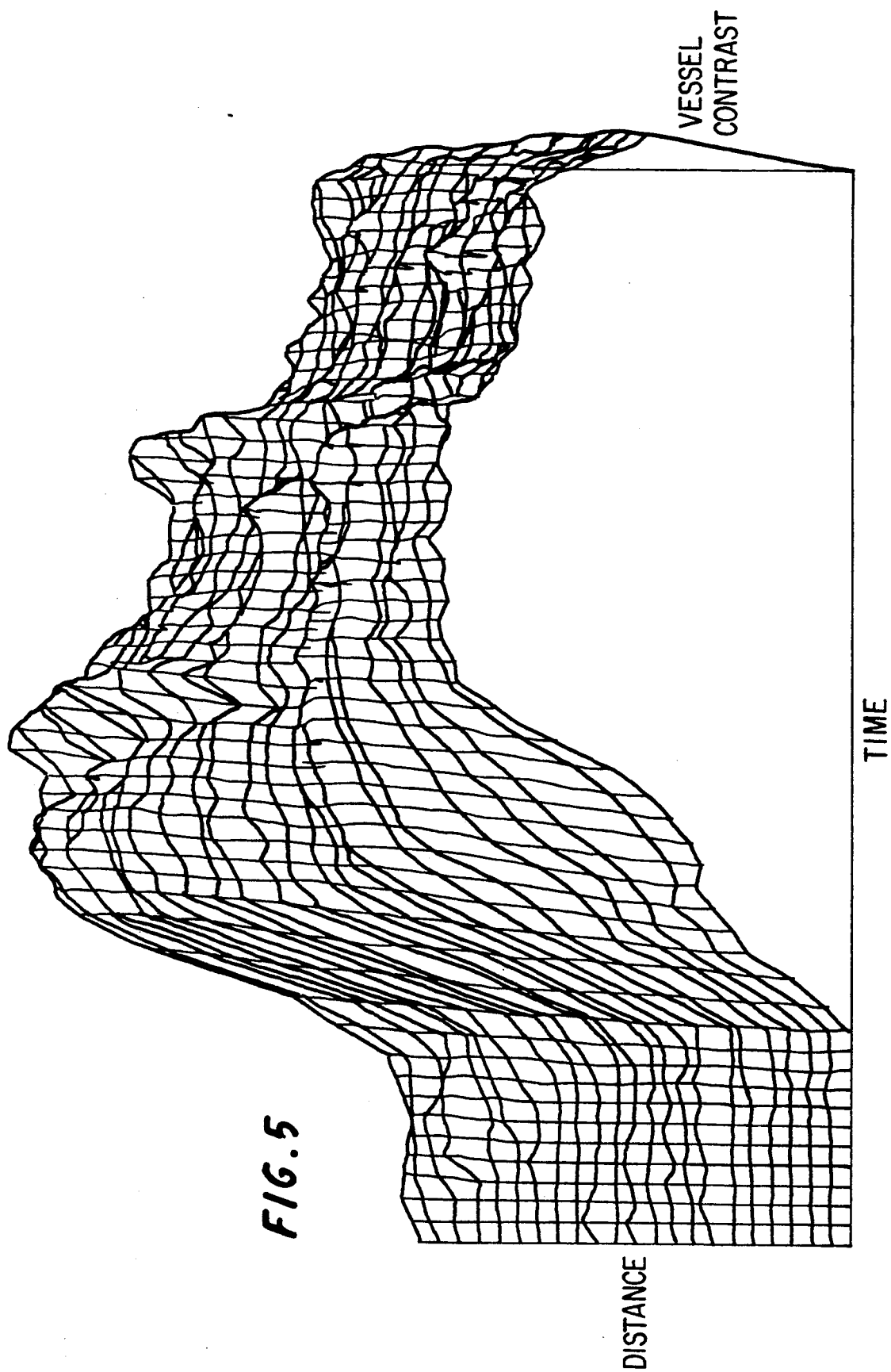
FIG. 5 is a graph illustrating variations of vessel contrast with time (time-density curves) and distance (distance-density curves) along the vessel segment during the time of image acquisition.
Figure 10:
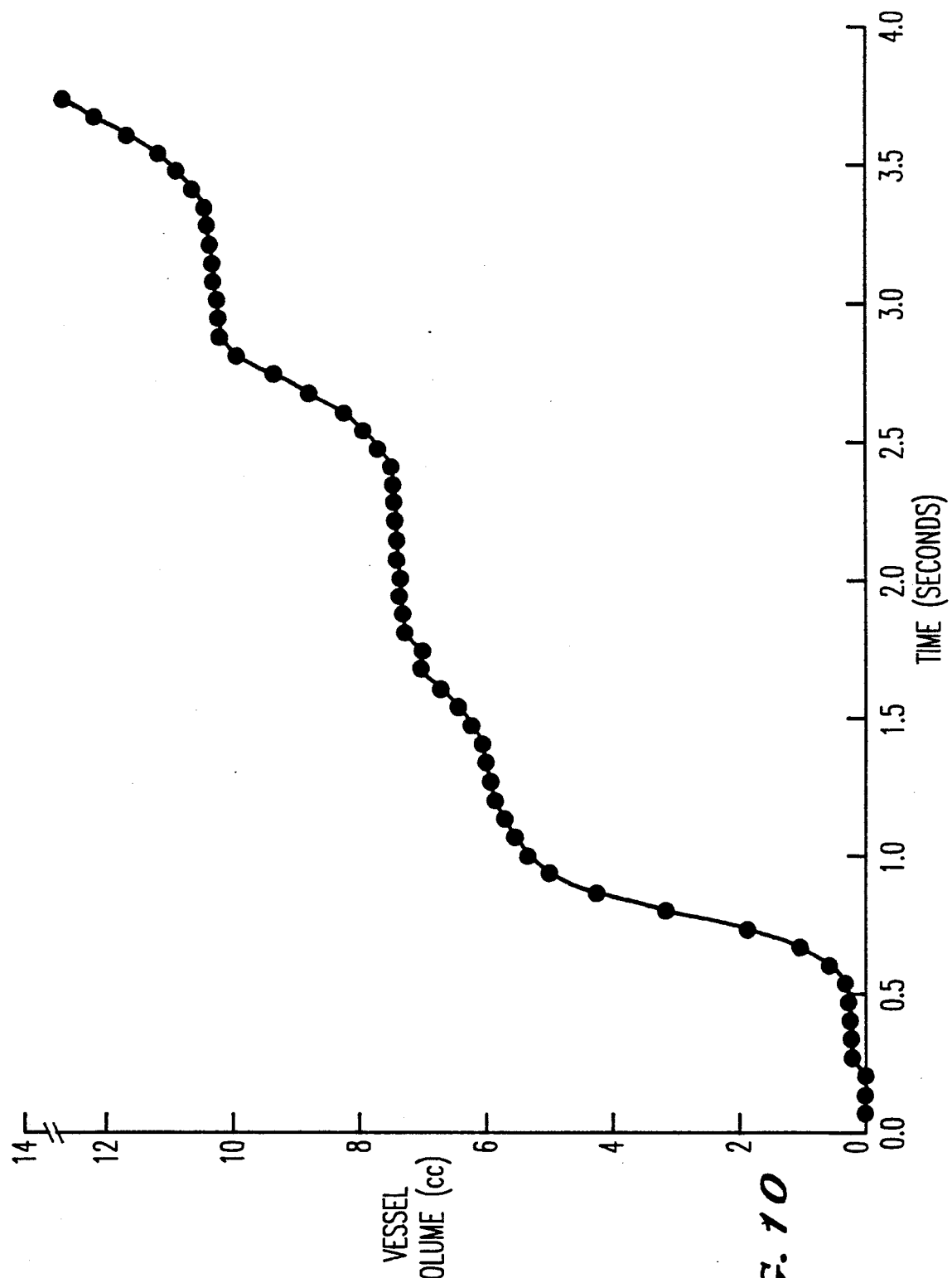
FIG. 10 is a graph illustrating a cumulative-volume-versus-time curve for pulsatile flow with an average flow rate of 3.5 cc/sec.
Figure 11:
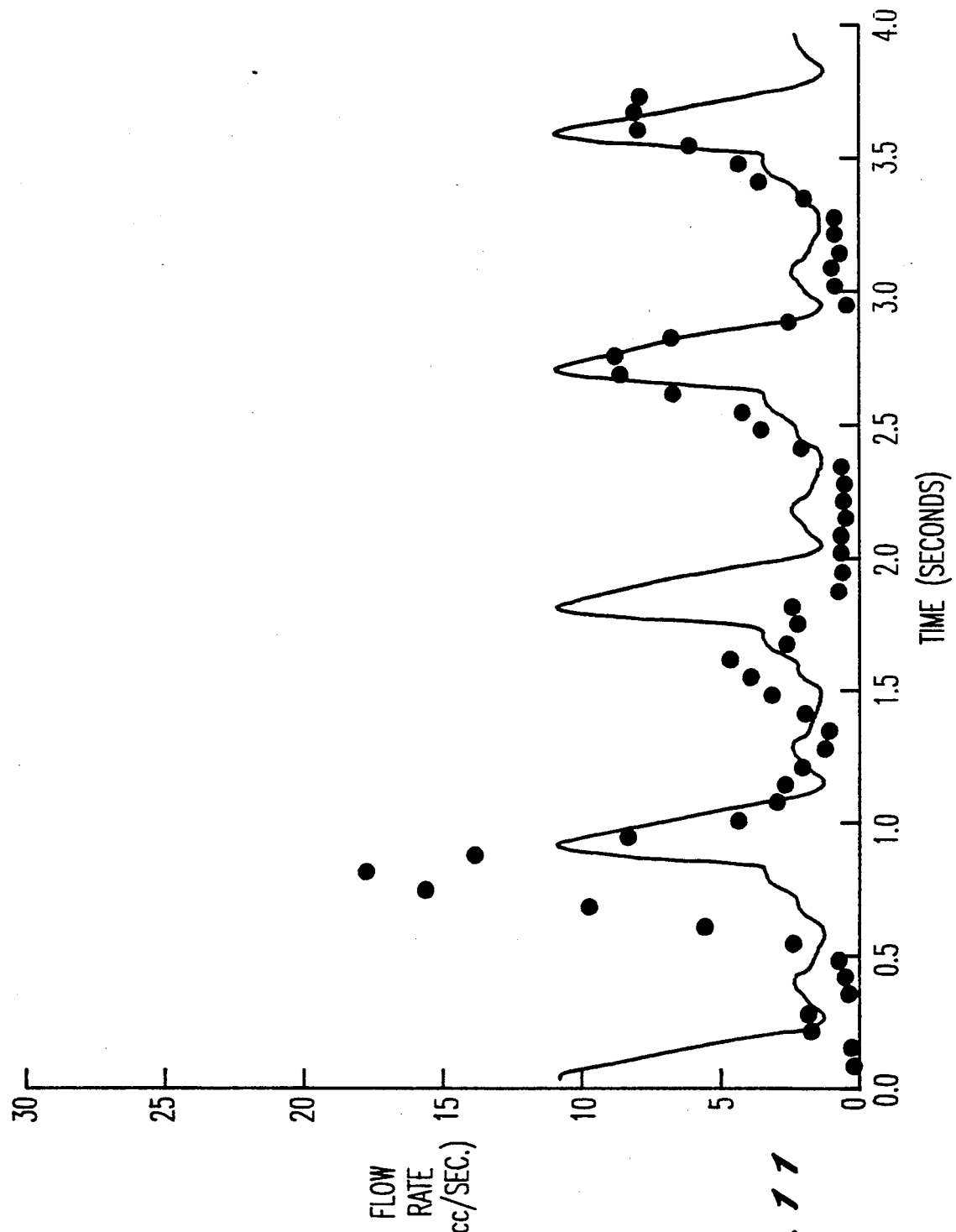
FIG. 11 is a graph comparing the instantaneous flow rates calculated using the distance-density curves and those measured with an electromagnetic flow meter, in which the flow rate averaged over one pulse cycle was 3.5 cc/sec.

FIG. 11 shows the instantaneous flow rates (circles) calculated from the cumulative-volume-vs-time curve (FIG. 10). The average flow rate over one pump cycle was 3.5 cc/sec for this study. The flow rates were calculated from slopes obtained from linear fits of three adjacent points. For comparison, the flow rates measured by the electromagnetic flow meter, shown in FIG. 4, are plotted here as the solid line. For the third and fourth pulse, the "instantaneous" flow rates measured according to the present invention appear to agree well with those obtained by the electromagnetic flow meter.

Figure 12:
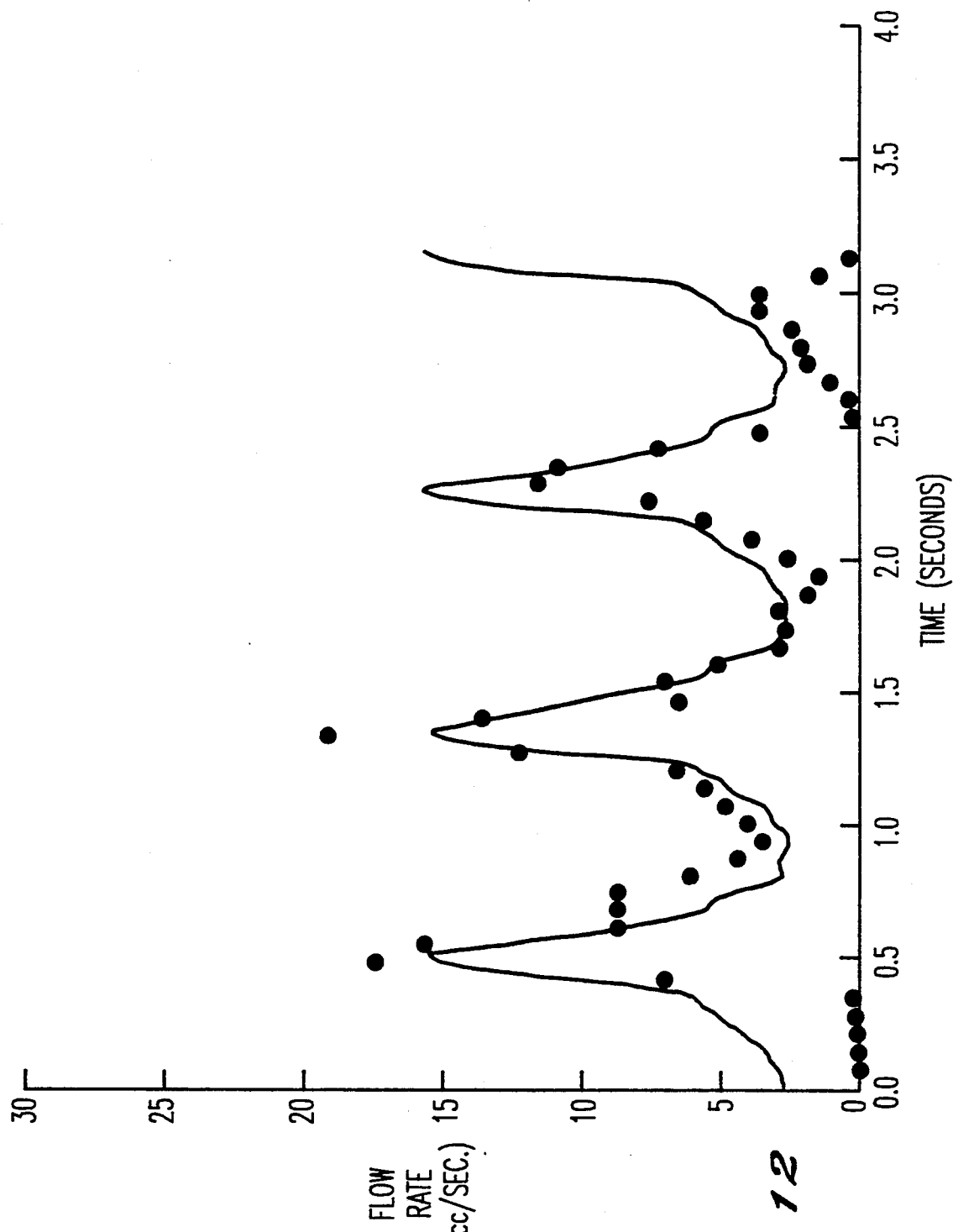
FIG. 12 is a graph comparing the instantaneous flow rates calculated using the distance-density curves and those measured with an electromagnetic flow meter, in which the flow rate averaged over one pulse cycle was 6.8 cc/sec.
Figure 13:
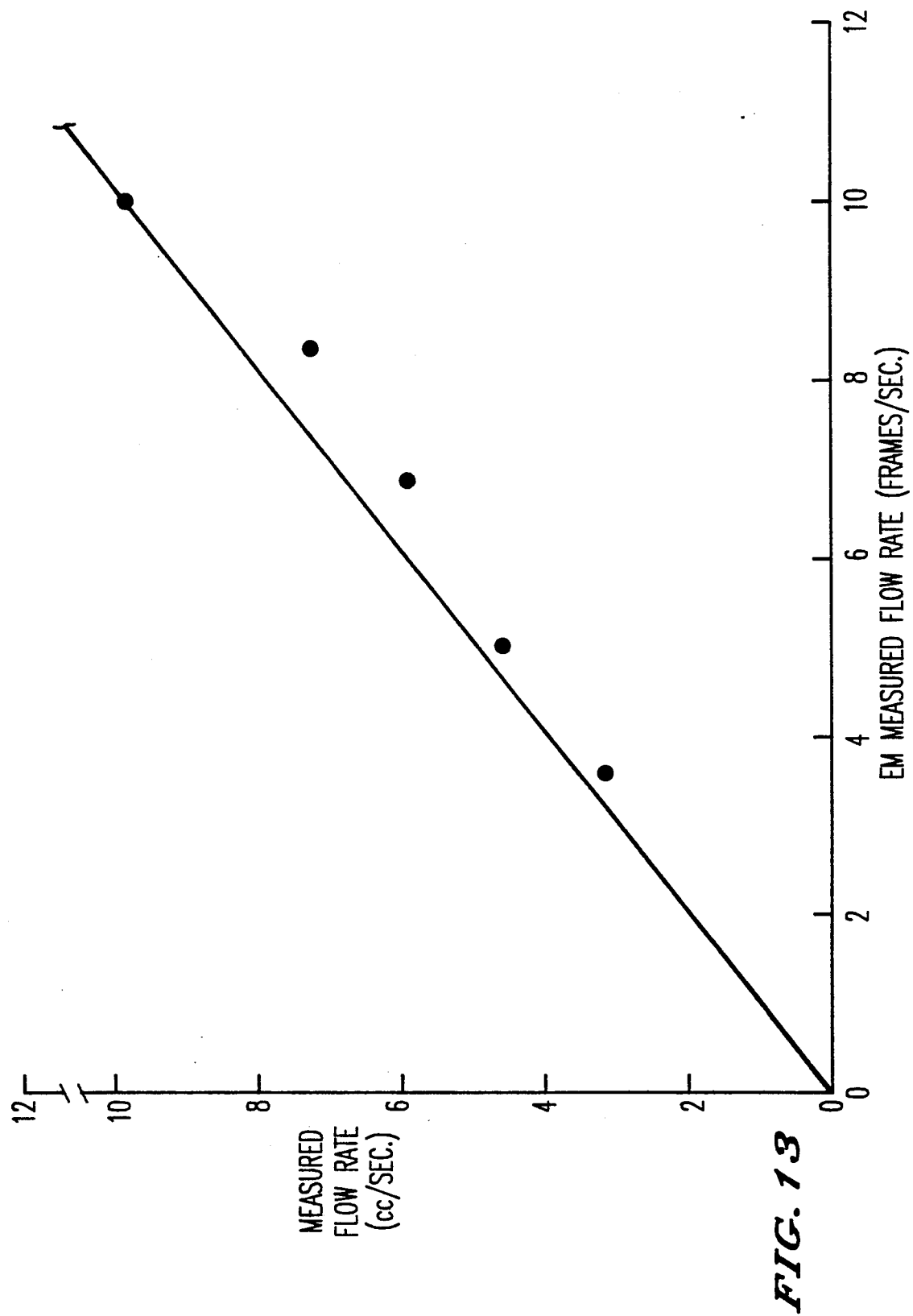
FIG. 13 is a graph comparing the average flow rates calculated using the distance-density curves and those measured with an electromagnetic flow meter.

Similar agreement has been obtained from studies performed at high flow rates, as illustrated in FIG. 12 in which the average flow rate was 6.8 cc/sec. The circles indicate the flow rates determined using the present invention, and the solid lines indicate the flow rates measured with the electromagnetic flow meter. Note that even for peak flow rates as high as 15 cc/sec, good agreement is apparent. Although poor agreement of the flow rates for some of the pulse cycles is seen, the average flow rates determined using the two methods agree well as shown in FIG. 13. For each study, the average flow rate was calculated from the slope of the straight line which best fit the entire cumulative-volume-vs-time curve.

It has been found that the peak flow rate of the first pulse determined by the method of the present invention tends to be approximately twice the actual peak flow rate. This result is possibly due to effects of laminar flow. In the case of laminar flow in an incompressible fluid with no flow at the vessel walls, the profile of the flow velocity across the vessel lumen is approximately parabolic, and the velocity at the center of the vessel is twice the average velocity across the lumen. The contrast material imaged in an angiogram is considered to move with the velocity of the blood of the region that it occupies. Thus, flow rates calculated from angiograms will be the flow rates for blood in those portions of the vessel lumen containing contrast material. Therefore, if the contrast material occupies the central portion of the vessel, calculated flow rates could be approximately twice the average flow rate in the vessel. Similarly, if the contrast material occupies the region near the vessel wall, the calculated flow rates are expected to be less than the average flow rate in the vessel. Thus, if the contrast material occupies different regions of the vessel lumen during the pulse cycles, it is expected that the calculated flow rates would change from pulse to pulse, as is seen in the data presented herewith. Therefore, these results also indicate that the method of the present invention offers the potential to measure the flow rate at any location across the vessel lumen (in particular, the center of the vessel), as well as the average flow rate across the vessel, as a function of time.

Figure 14:
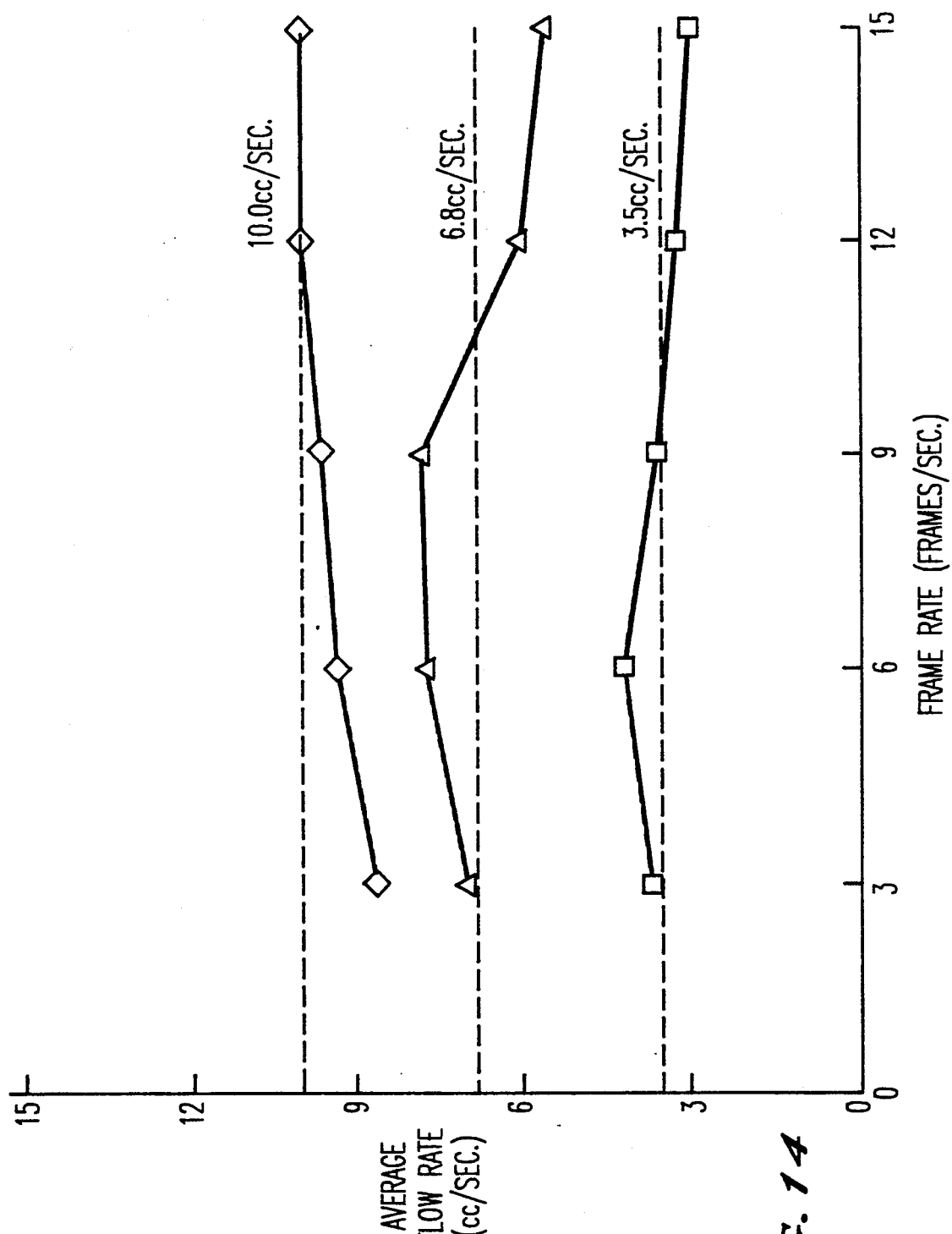
FIG. 14 is a graph illustrating the calculated average flow rate versus simulated frame rate of image acquisition.
Figure 15:
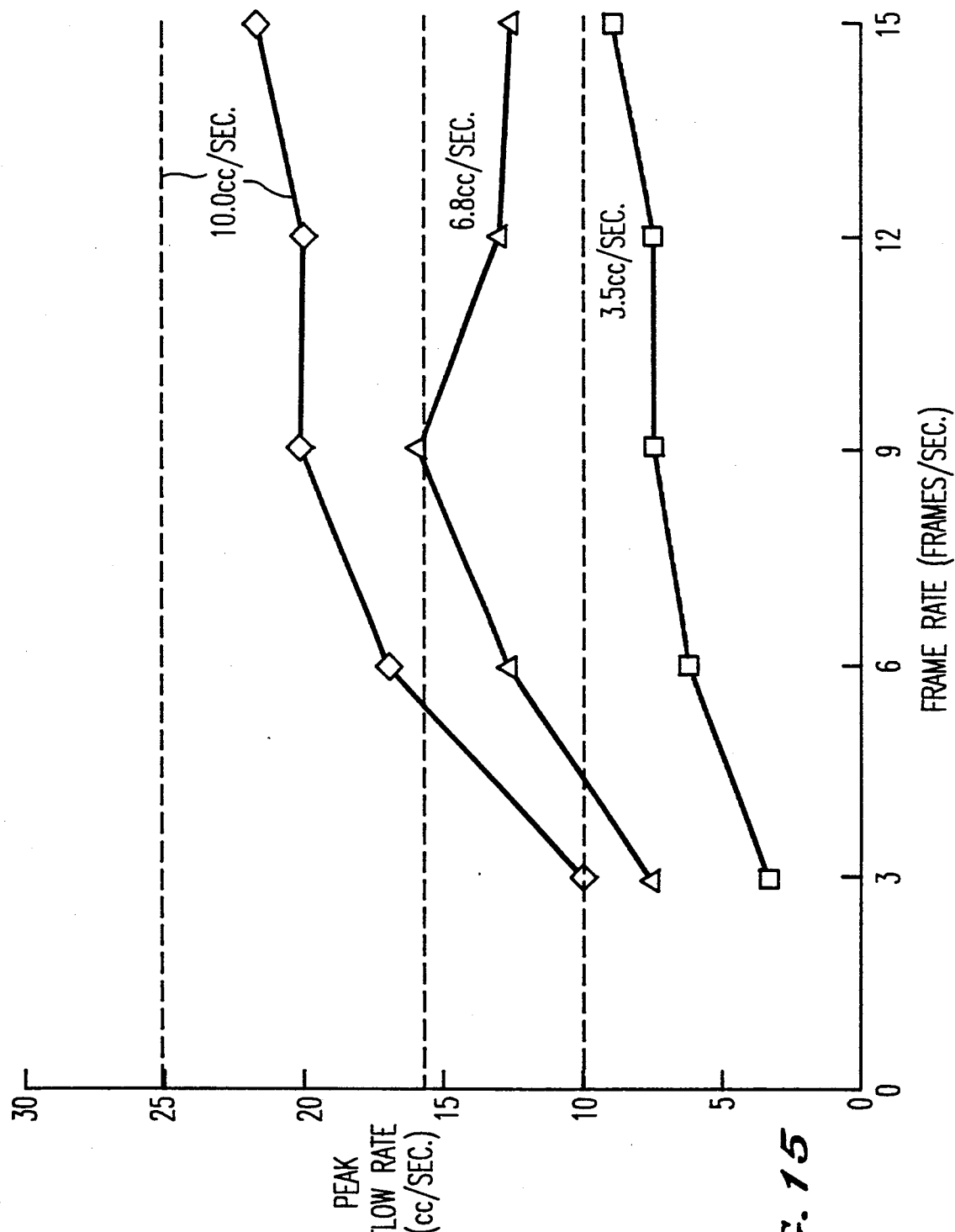
FIG. 15 is a graph illustrating the calculated peak flow rate versus simulated frame rate of image acquisition.

In clinical practice, images are acquired often at frame rates lower than 15 frames/sec. For the evaluation of the accuracy of the present method at low frame rates, images at low frame rates were calculated, as a simulation study, from images which were acquired at 15 frames/sec by averaging vessel contrast over a number of frames. In FIG. 14, the calculated average flow rates for average flow rates of 3.5, 6.8, and 10 cc/sec are plotted as functions of the frame rate employed. The dashed lines indicate the average flow rates measured using an electromagnetic flow meter. Note that for frame rates greater than 6 frames/sec, the calculated flow rates are within 10% of the average flow rates measured using the electromagnetic flow meter. It should be noted that the effective temporal averaging occurring at lower frame rates affects the accuracy of the calculated "instantaneous" flow rates. In FIG. 15, the peak calculated flow rates for average flow rates of 3.5, 6.8, and 10 cc/sec are plotted as functions of frame rate. The peak flow rates as measured by the electromagnetic technique are indicated by the dashed lines. It is apparent that as the frame rate decreases the calculated value for peak flow decreases in general and deviates considerably from the peak flow rate measured with the electromagnetic technique.

Figure 16:
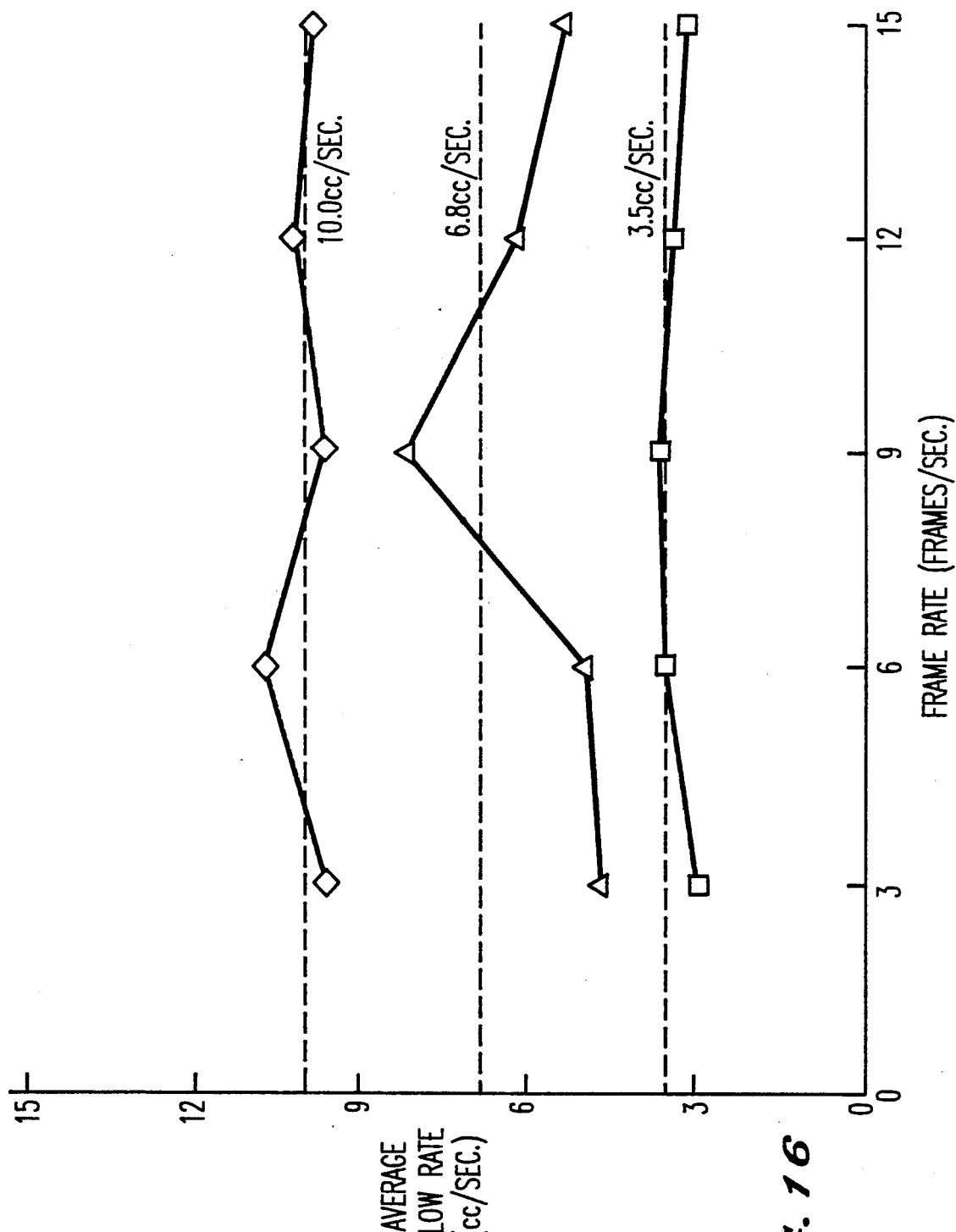
FIG. 16 is a graph illustrating the effect of interpolation by means of a plot of the calculated average flow rate versus simulated frame rate of image acquisition, in which low-frame-rate) data were interpolated to generate simulated 15 frames/sec data.

For low frame rates and high flow velocities, the distance that the bolus travels between acquisitions can be greater than the length of the vessel segment used for correlations between acquisitions, and the cross-correlation of the distance-density curves will most probably yield underestimates of the true flow velocity. These underestimated flow velocities would then result in a reduction in the instantaneous and average flow rates calculated from images obtained at low flow rates. However, by calculating "high-frame-rate" images by interpolation of low frame rate images, the distance traversed by the bolus between each "acquisition" would be decreased and the accuracy of the correlation can be increased. To generate "high-frame-rate" data, additional points on the time-density curve for each location in the vessel are calculated using curve fitting and interpolation. From these data, additional distance-density curves are calculated for times between actual acquisitions. Using this approach, 15 frame/sec "images" were generated from images "acquired" at low frame rates. Note that the low-frame-rate images used here were calculated in the earlier simulation study by temporal averaging of images acquired at 15 frames/sec. In FIG. 16, average flow rates which were calculated using the interpolated 15 frames/sec data are plotted as functions of the frame rate for the "acquired" images. Comparison of the results for high flow rates (e.g., 10 cc/sec) in FIGS. 14 and 16 indicates that calculated average flow rates agree well with results obtained with the electromagnetic flow meter, especially for low-frame-rate acquisitions, when interpolation is employed for simulation of higher frame rates.

Figure 17:
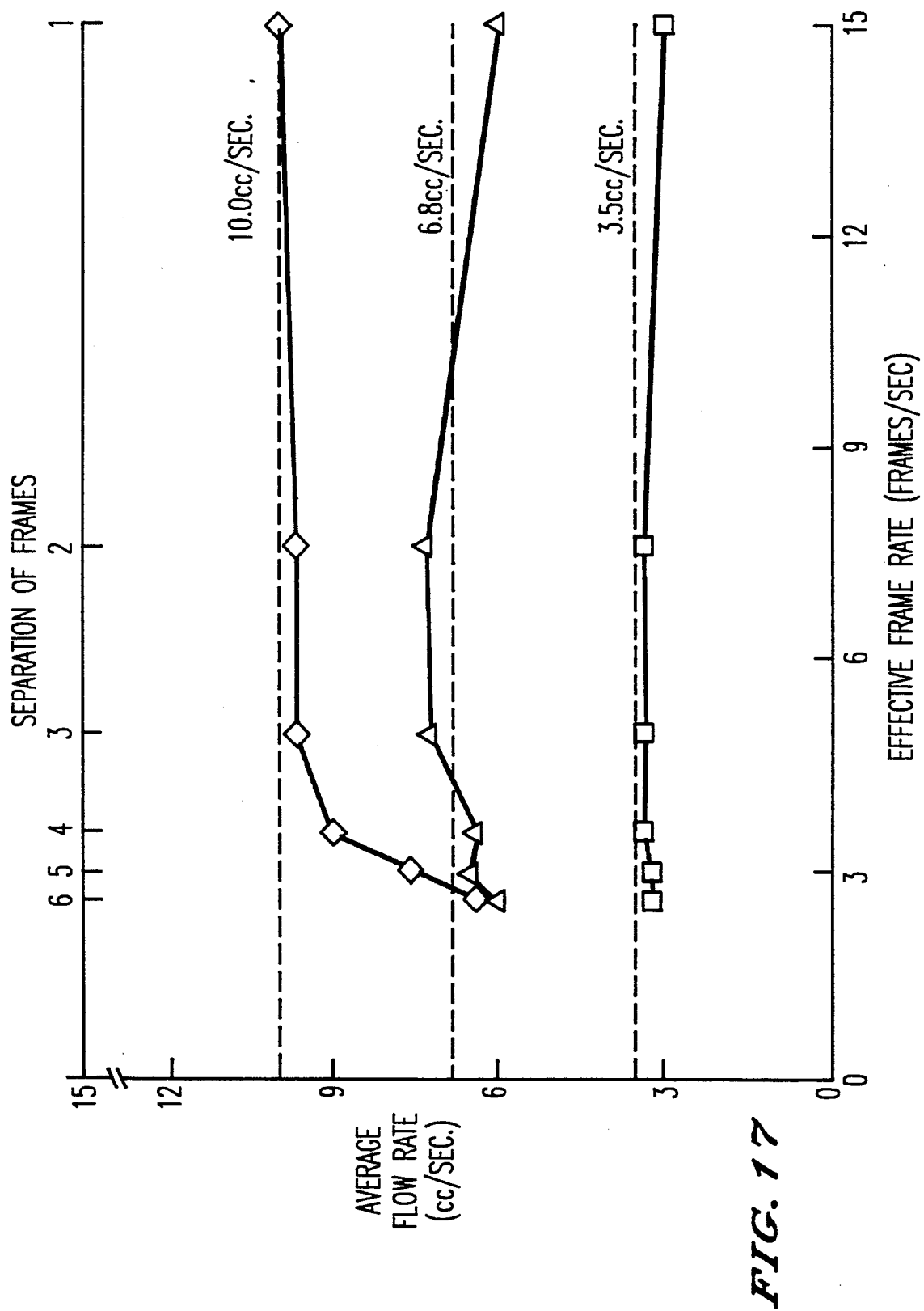
FIG. 17 is a graph illustrating the effect of time interval between frames on the calculated average flow rates.

As was stated above, in the step of determining the distance traversed by the bolus, the images from which the distance-density curves are obtained may be separated by more than one acquisition interval. The results discussed above were obtained using a temporal separation of one acquisition interval for the correlation of images. When larger separations are employed, results are expected to be similar to those obtained when the frame rate is reduced. In FIG. 17, for comparison with the previous average flow rate data, the average flow rates are plotted versus the "effective" frame rate, which is obtained by dividing 15 by the number of frames for separation. The calculated flow rates agree well with the average flow rates measured using the electromagnetic flow meter for separations up to 6 frames for the 3.5 and 6.8 cc/sec data and for separation up to 3 frames for the 10 cc/sec data, respectively.

The precision of the calculated flow rates will be determined by the distance between points in the distance-density curves and the temporal separation between the images employed. For periods of low flow rate during the pulse cycle, large separation between points or short time intervals will lead to less precise (and perhaps less accurate) flow rates. Thus, use of more frequent sampling of the vessel contrast (or interpolation) along the vessel or larger temporal separations between images can improve the precision (and perhaps the accuracy) of calculated flow rates for periods of low flow rate.

Figure 18:
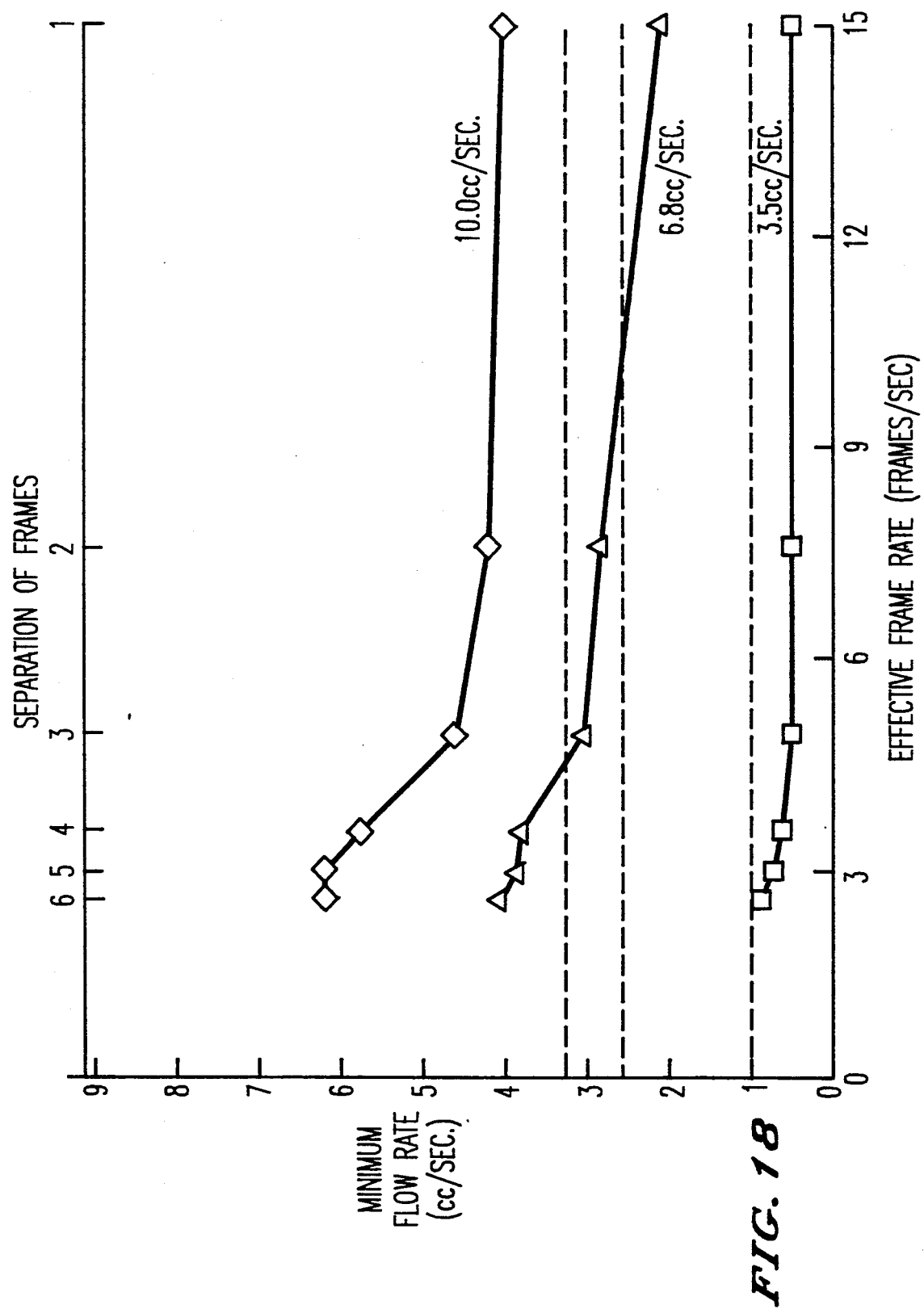
FIG. 18 is a graph illustrating the effect of time interval between frames on the calculated minimum flow rates.

From the flow rate calculated using frame separations from one to six frames, the minimum flow rates were obtained and are plotted in FIG. 18 versus the "effective frame rate". The minimum flow rates determined using the electromagnetic flow meter were approximately 1, 2.5, and 3.2 cc/sec for the average flow rates of 3.5, 8,3 and 10 cc/sec, respectively. For low flow rates, it is apparent that results obtained using a temporal separation of two or three acquisition intervals are more accurate than those calculated using one, or 4 or more intervals. Thus, the most accurate instantaneous and average flow rates could be calculated using separations of one acquisition interval for calculation of the peak flow rates and two or three acquisition intervals for calculations of flow rates during the low-flow-rate period of the pulse cycle.

EMBODIMENTS

Embodiment 1

For vessels which do not move during image acquisition, the blood flow rates can be determined using opacified images obtained with a DSA system where the centerline of the selected vessel segment is indicated by the user. Vessel segments between branches are chosen because the flow rate may be considered to be constant between branches. A smooth centerline curve is generated from the indicated centerline by curve fitting.

The vessel size is determined from an opacified image using image data which lie along lines perpendicular to the vessel centerline. For vessels much larger than the width of the line spread function of the imaging system (approximately 1 mm for most systems), the vessel size along the length of the vessel is measured using a weighted sum of the edges determined by first and second derivative techniques.

Figure 19:
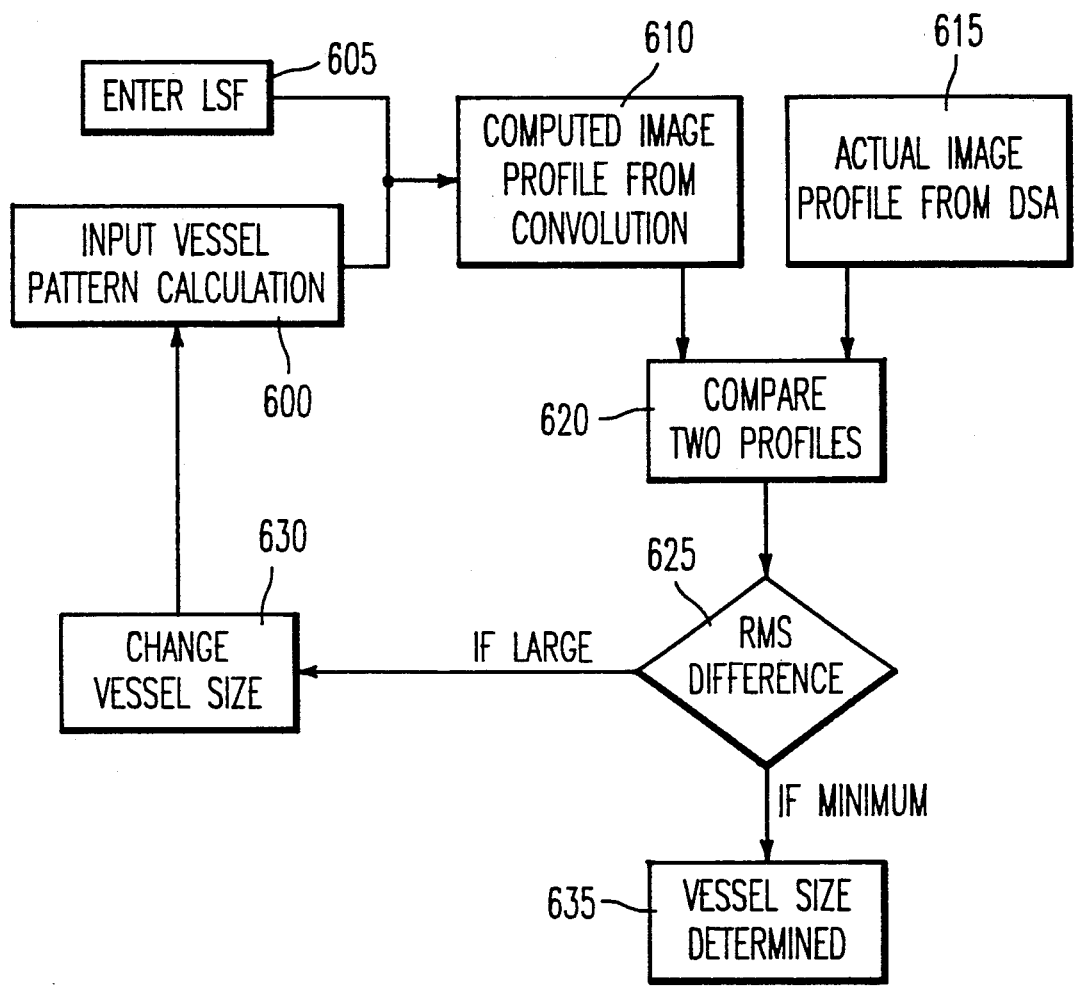
FIG. 19 is a flow chart illustrating the iterative deconvolution processing performed according to the present invention.

For vessels with sizes comparable to or smaller than the width of the line spread function of the imaging system from which the digital X-ray images were obtained, the vessel size is determined using the iterative deconvolution technique, shown in the flow chart of FIG. 19, and described in the above noted article by Fujita et al. In the iterative deconvolution technique, the "true" vessel size is obtained from a blurred vessel image by taking into account the line spread function (LSF) and characteristic curve of the imaging system from which the digital X-ray images are obtained. At step 600, an input vessel pattern is calculated using the assumption that a parallel X-ray beam is incident on a cylindrical vessel filled with contrast material. The LSF of the imaging system is entered (step 605) and is convolved at step 610 with the input vessel pattern calculated in step 600. An actual image profile is obtained from the angiogram (step 615) and is compared iteratively, at step 620, with the computed image profile resulting from the convolution. The RMS (root-mean-square) difference between the two profiles is then determined at step 625. In step 630, the vessel size is changed, until the RMS difference between the two profiles is minimized. At that point, in step 635 the size of the cylindrical vessel yielding the best matched profile is considered the best estimate of the unknown vessel size. From a comparison of measured diameters with the nominal diameters of iodine-filled plastic tubes, it was found that the accuracy and precision of this technique were approximately 0.1 mm over the range of vessel sizes from 0.5 mm to 7.0 mm (see Fujita et al.).

For vessels oriented parallel to the imaging plane, the measured vessel-image size is corrected for magnification, and the cross-sectional area of the vessel is calculated from the corrected vessel size using a circular cross-section model. The magnification is determined using calibration devices, such as catheter tip, balls, or rods of known diameter. Other techniques for determination of vessel cross-sectional area may be used, such as densitometric technique (See Kruger et al: "Estimation of the Diameter and Iodine Concentration Within Blood Vessels Using Digital Radiographic Devices", Med. Phys. 8:652 (1981) in conjunction with a calibration device.

The distance-density curve in each image of the acquired image sequence is obtained using vessel contrast (i.e., the difference between pixel value at the center of the vessel and the pixel value in the background) for each pixel along the vessel centerline.

When images are acquired at frame rates of 15 or more per second, the distance traversed by the bolus of contrast material between image vessels is determined by cross-correlation of the distance-density curves obtained from adjacent frames. The cross-correlation technique employs the root-mean-square (RMS) difference between the two curves. One curve will be shifted spatially until the shift which yields the minimum RMS difference is determined. Instead of the RMS difference, other indices, such as absolute difference or weighted difference, may also be used.

Note that an alternative method of using the distance-density curve is the analysis of the volume-density curve. For vessels which significantly change size in the region of analysis, the distance-density curves may not give accurate results. In this case, the volume-density curves will be employed to determine the volume traversed by the blood between image acquisition. The volume-density curve expresses the relationship between the density of contrast material in the vessel and the cumulative volume along the length of the vessel. The cumulative volume along the vessel is obtained by a summation of the vessel volumes between locations in the vessel. The vessel volumes are calculated as the product of the local vessel cross-sectional area and the distance between these locations.

When distance-density curves are employed for the correlation, the cumulative-volume curve is calculated by multiplying the determined cumulative-distance curves by the average cross-sectional area of the vessel. The average cross-sectional area is calculated by averaging the values of the cross-sectional area obtained along the length of the vessel.

The flow rates are calculated from the cumulative-volume-vs-time-curve by fitting sets of three points with a straight line. The slope of the straight line corresponds to the flow rate for the time corresponding to the central point. However, higher order polynomial curves may be used for fitting the data points in order to estimate the instantaneous slope.

Embodiment 2

For vessels which do not move during image acquisition but which are not parallel to the imaging plane, the vessel centerline and vessel size are determined as described in Embodiment 1.

The determined vessel size will be corrected for magnification and the cross-sectional area of the vessel will be calculated from the corrected vessel size using a circular cross-sectional model. For vessels which are oriented parallel to the imaging plane, calibration devices are used, such as catheters, balls, or rods of known diameter. However, if the orientation of the vessel is not parallel to the imaging planes or changes along the length of the vessels, the magnification changes. Therefore, stereoscopic (See Fencil et al, Invest Radiol. 23:33 (1988), supra) or biplane imaging (See Potel et al: "Methods For Evaluating Cardiac Wall Motion in Three Dimensions Using Bifurcation Points of the Coronary Arterial Tree", Invest. Radiol. 18:47 (1983)) techniques are employed to determine the magnification and orientation of the vessel along the length of the vessel. It should be noted that when biplane techniques are employed, the vessel cross-section area may be calculated using an elliptical model for the vessel lumen in which the vessel sizes measured in each image are taken as the lengths of the major and minor axes of the ellipse.

The distance-density curves are obtained as described in Embodiment 1. However, a correction factor for the orientation is applied to the data. The correction of orientation is important for obtaining accurate results from the correlation technique which is based on the assumption that the relationship between the concentration of contrast material in the vessel and the vessel contrast determined in the image is constant along the vessel For vessel segments which are not parallel to the imaging plane, e.g., lie at an angle with the imaging plane, the measured vessel contrast is divided by the cosine of the angle.

Another approach for making the correction for orientation is based on the assumption that contrast material is conserved, i.e., that the total amount of contrast material passing by each location in the vessel is a constant when integrated over time in all the images. Thus, the correction for orientation can be made by dividing the vessel contrast at each location by the integral of the time-density curve at that location. If the entire washout of the bolus is not imaged, the missing washout is estimated by using an exponential extrapolation method or any similar curve fitting method. The integral is calculated using the available data and also the extrapolated portion of the curve. After this correction, distance-density curves are expected to be directly related to the distribution of the concentration of the contrast material along the length of the vessel.

For frame rates of 15 or more per second, the correlation techniques described in Embodiment 1 are employed to calculate the cumulative-distance curves, from which the cumulative-volume curves and flow rates will be calculated as described in Embodiment 1.

Embodiment 3

For vessels which move during image acquisition, it is difficult and time consuming to select accurately corresponding vessel regions in a sequence of angiograms. As a result, the accuracy of calculated blood flow rates can be diminished. Previous investigators either have assumed that the vessel does not move or have relied on the operator's placement of ROIs to perform blood flow analysis.

Figure 20:
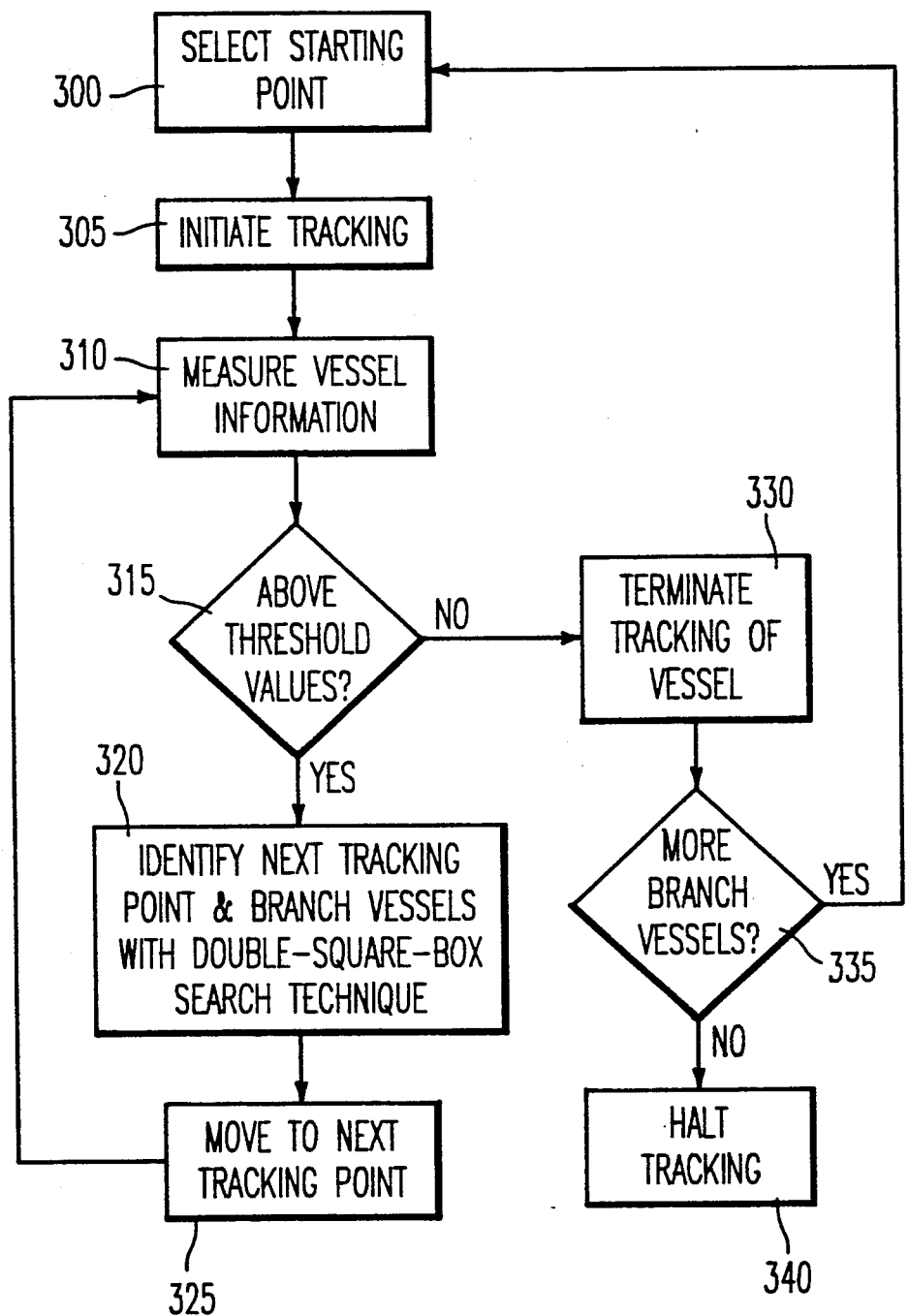
FIG. 20 is a flow chart illustrating the double-square-box tracking method employed according to the present invention.

For automated and reliable determination of vessel locations and quantification of the vessel information, i.e., the vessel size, contrast, and centerline position, in each angiogram, the double-square box method for vessel tracking is employed (See Hoffmannet al: "Automated Tracking of the Vascular Tree in DSA Images Using a Double-Square-Box Region-of-Search Algorithm", SPIE 626:326 (1986)), as illustrated in FIG. 20. A starting point in the vessel to be analyzed will be selected by the user in one of the opacified images (step 300). Tracking will then be initiated (step 305) and then all information necessary for the flow rate calculations will be acquired automatically. For the starting point and subsequent tracking points, the pixel values along a line lying perpendicular to the vessel centerline at that location are obtained from the image data (step 310). From these data, the vessel size and contrast are obtained by means described in embodiment 1. If the vessel size and contrast are larger than preselected threshold values as determined at step 315, the region around that point is searched for the next tracking point and also for branch vessels; this is accomplished by using a double-square-box region-of-search algorithm (step 320), as described in detail below in relation to FIG. 21. If branch vessels are located, their starting points are stored for later use (see FIG. 21 — step 415). The tracking then proceeds to the next tracking point determined by the search algorithm (FIG. 20 — step 325). The tracking of a vessel continues until either the local vessel size or the local vessel contract is below the respective predetermined threshold value, tracking of that vessel is then terminated (step 330). After a vessel has been tracked, its branches are tracked in the same manner by searching for stored starting points of branch vessels which have not been tracked (step 335). Tracking therefore continues until all connected vessels which satisfy the threshold criteria in that vascular tree are tracked. After all vessels have been tracked, the tracking is halted (step 340). When tracking is completed, the vessel information is available for further quantitative analysis.

Figure 21:
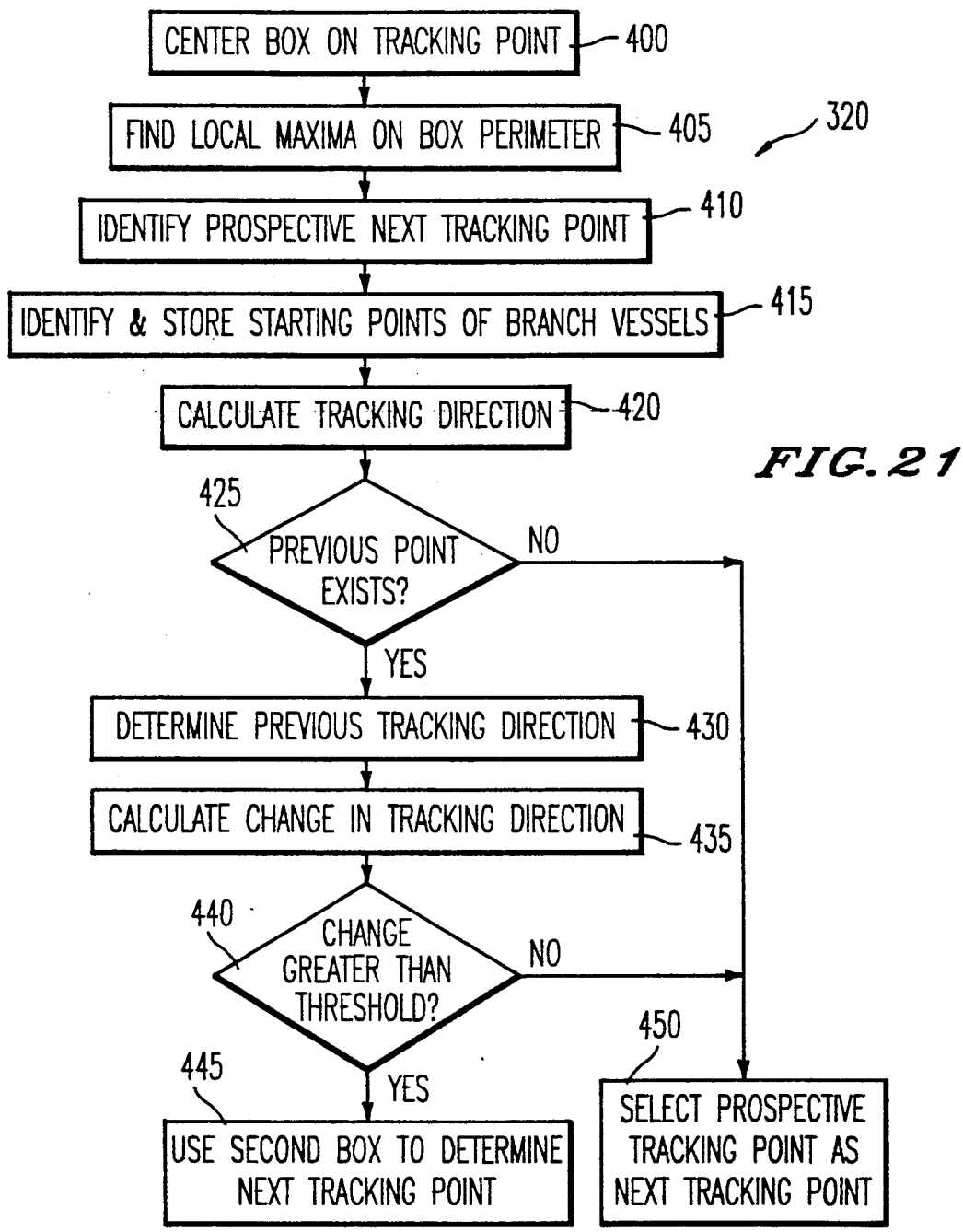
FIG. 21 is a flow chart illustrating the region-of-search steps performed in the double-square-box tracking method shown in FIG. 20.

The tracking points in vessels and their branches are located by means of the double-square box region of search (FIG. 20 — step 320) in the following manner. Referring to FIG. 21, a large square box is centered on the tracking point in the vessel being tracked (step 400). The width of the box is equal to twice the size of the vessel at that location. The sides of the box are parallel to the x and y axes in the image. The pixel values of the pixels of the large box are examined in order to locate local maxima (step 405). The segment on the perimeter which overlaps the previously tracked portion of the vessel is excluded from the search for the maxima in order to prevent backtracking. The pixel with the maximum pixel value is taken as the prospective next tracking point (step 410). The other maxima are stored as starting points of branch vessels of the vessel being tracked (step 415). After the prospective next tracking point is determined, the direction of tracking is calculated as the vector from the center of the box, i.e., the present tracking point, to the prospective next tracking point (step 420). However, if the tracking direction changes by more than the preset threshold angle, a second small square box is employed to determine the next tracking point (step 445). If not, the prospective tracking point is selected as the next tracking point (step 450).

Figure 22:
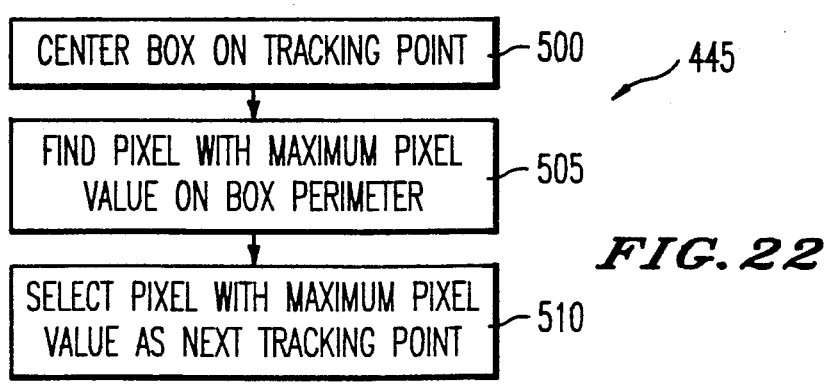
FIG. 22 is a flow chart illustrating further "second square box" processing in the determination of a next tracking point in the method of FIG. 20.

FIG. 22 illustrates steps performed in step 445 of FIG. 21. The second square box is first centered on the tracking point (step 500). The width of the second square box is equal to the vessel size at that location. The sides of the box are parallel to the x and y axes in the image, and the segment of the perimeter which overlaps the previously tracked portion of the vessel is again excluded from the search. The perimeter of the second box is searched for the pixel with the maximum pixel value (step 505); this pixel is selected as the next tracking point (step 510). The large box, with a width equal to twice the local vessel size in the image, provides efficient tracking in the relatively straight regions of vessels. The second, small box, with a width equal to the local vessel size, provides accurate tracking in the curved regions of the vessels.

The tracking points are separated by a number of pixels. Therefore, the distance-density curves are obtained from the vessel contrast data determined by tracking using curve-fitting and interpolation techniques in order to improve the precision of the distance measurements. By using the tracking data to identify pixels lying along the centerline, the distance-density curves may also be determined on a pixel-by-pixel basis.

For calculation of flow rates, data acquired at locations separated by 7 to 15 pixels have been employed and no difference was found in the calculated flow rates. In addition, no difference in the calculated flow rates was observed for distance-density curves calculated using two different orders of polynomial fits. Therefore, it is expected that accurate results from distance-density curves can be determined on a pixel-by-pixel basis based on those determined using the tracking data.

If the specified vessels move during image acquisition, their magnification and orientation relative to the imaging plane can change. Therefore, in the case of vessel motion, corrections for magnification and orientation are applied to the data in each frame as described in Embodiment 2. In addition, the corresponding vessel segments used for the blood flow analysis in different frames are identified by comparing the vessel information obtained from tracked angiograms by means of the double-square-box method. For frame rates of 15 or more per second, the correlation techniques described in Embodiment 1 are employed to calculate the cumulative-distance curves, from which the cumulative-volume curves and flow rates are calculated as described in Embodiment 1.

Embodiment 4

If low frame rates are employed for image acquisition, e.g., 6 or less, the accuracy of the measured average flow rates is improved by generating interpolated high-frame-rate data using the vessel contrast obtained from the acquired images.

The vessel centerline, vessel contrast, and vessel size and distance-density curves are determined from the acquired images as described in Embodiments 1-3.

To derive distance-density curves for high frame rates from distance-density curves obtained at low frame rates, additional points on the time-density curve for each location in the vessel will be generated using curve fitting and interpolation. From these data, additional distance-density curves will be generated, thus providing a high frame rate simulation. The correlation techniques described in Embodiments 1 and 3 will be employed to calculate the cumulative distance curves, from which the cumulative-volume curves will be generated as described in Embodiments 1-3. The flow rates will be calculated from the cumulative-volume curves as described in Embodiment 1.

Embodiment 5

The vessel centerline, the distance-density curves, and the vessel cross-sectional area will be determined using the techniques for stationary and non-stationary vessels described in Embodiments 1-4.

In order to improve precision and accuracy of the flow rate calculations for periods of low flow rates during the pulse cycle, the distance that the bolus traverses between image acquisitions will be determined using separations of one, two, and three frames, i.e., (referring to FIG. 9) J will be equal to "I+1", "I+2", or "I+3". The time coordinate of the cumulative-distance will be "(I+J)/2" multiplied by the inverse of the frame rate. The data which have the same time coordinates will be averaged, e.g., the data obtained using frames 2 and 3 with a separation of one frame and the data obtained using frames 1 and 4 with a separation of 3 frames. The data from all three calculations will be combined to yield one cumulative-distance curve. Note that the time coordinates of the cumulative-distance and cumulative-volume data will be separated by one-half the inverse of the frame rate.

The cumulative-volume curves will be obtained by multiplication of the cumulative-distance data by the cross-sectional area of the vessel, as described in Embodiments 1-3. The flow rates will be calculated from the cumulative-volume curves as described in Embodiment 1.

Figure 23:
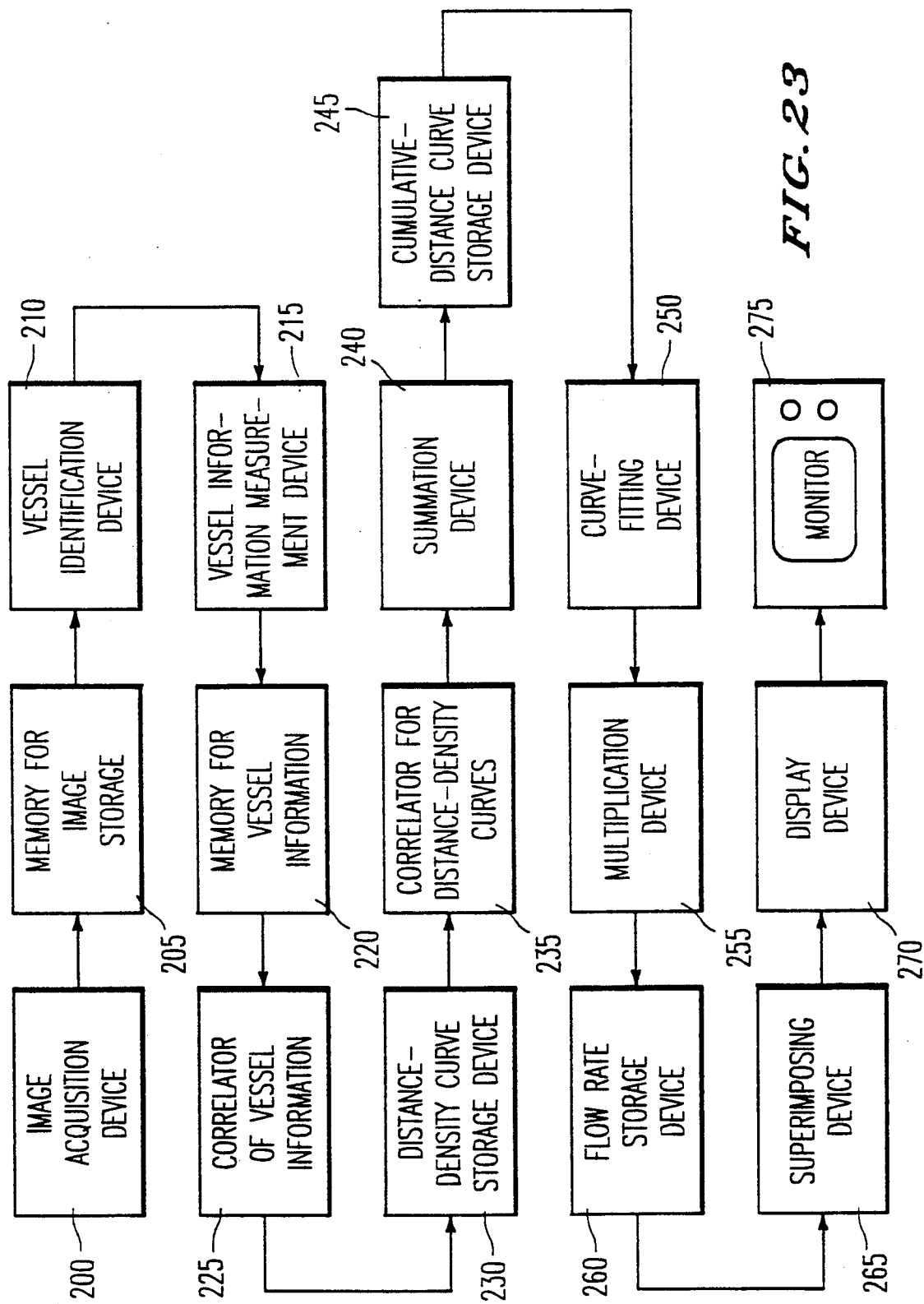
FIG. 23 is a schematic block diagram of the system of the invention.

Referring now to FIG. 23, there is shown a more detailed functional block diagram illustrating the system of the invention. In FIG. 23, x-ray measurements of an object are obtained from an image signal generator 200, for example, the output of a television camera in a fluoroscopic or angiographic system. The image signal is applied to a first memory 205 where the original images are stored. Memory 205 feeds its contents to a vessel identification device 210 which consists of a program in hardware or software which identified the starting point in an opacified vessel either by assisting user identification or by searching the image for an opacified vessel. Functionally coupled to the device 210 is a device for measurement of vessel information 215 which is a program in hardware or software which implements the double-square box tracking technique for identifying the vessels in the images starting with the starting point in an opacified vessel in each image. This program performs a differentiator function and an iterative deconvolution technique for determination of vessel information as the vessels are tracked. The vessel information determined with device 215 is stored in the memory device 220 which is a second memory within a computer which includes memory device 205 or it could be memory associated with another computer. The storage capacity would need to be approximately 2 Megabyte, thus, a relatively small computer such as an IBM/PC could be employed.

Functionally coupled to the memory 220 is a correlator of vessel information 225 which consists of a program in hardware or software for the determination of the relationships between the vessel information obtained in each of the images in order to identify images of the same vessels in the different images and to calculate the distance-density curves from the vessel information of the correlated vessels. The distance-density curves are stored in a third memory 230; memory requirements should be approximately 2 Megabyte.

Analysis of the distance density curves is performed by the correlator for distance-density curves 235 which consists of a program in hardware or software and which iteratively shifts one of a pair of distance-density curves and calculates a difference between the unshifted curve of the pair and the shifted curve of the pair until the difference between the curves is minimized, and then the program provides the distance which yielded the minimum difference. Functionally coupled to the correlator 235 is a summation device 240 which is an arithmetic program in hardware or software which sums the distances provided by correlator 235 in order to calculate the cumulative-distance curve. The cumulative-distance curves are stored in a fourth memory 245; memory requirements will be approximately 1 Kilobyte.

The cumulative-distance curves stored in memory 245 are applied to the curve-fitting device 250, which is a program in hardware or software and which fits the cumulative-distance curve stored in memory 245 with a curve and calculates the slope of the curve at a number of points for determination of instantaneous velocities of the blood in the vessel. The multiplication device 255 functionally coupled to the device 250 is an arithmetic program in hardware or software which multiplies the velocities determined by device 250 by the cross-sectional area of the vessel (determined by device 215 and stored in memory 220) in order to calculate instantaneous flow rates. The flow rates are stored in a fifth memory 260; memory requirements will be approximately 1 Kilobyte.

The superimposing device 265 is a program in hardware or software which superimposes calculated flow rate data on to a original opacified image for subsequent display. The display device 270 interfaces the superimposing device to the monitor 275, such as the Gould-/DeAnza image processor. The monitor 275 is a device for viewing the results of the blood flow analysis.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for automated measurement of instantaneous and average blood flow rates using a digital X-ray image, comprising the steps of:
   generating a sequence of digital X-ray images of an object as a contrast material is injected into the object;
   storing said images;
   identifying opacified vessels in each of said images;
   measuring selected vessel parameters, including vessel size, contrast, and position, of the opacified vessels identified in said identifying step;
   identifying the same vessel in different of said images;
   deriving vessel longitudinal density curves representing vessel contrast as a function of one of longitudinal distance or volume along the length of said vessel based on the measured vessel contrast;
   correlating said density curves from different images to measure one of distances or volumes traversed by said contrast material as a function of time; and
   calculating at least one of instantaneous and average flow velocities and flow rates in said vessels from the measured one of distances or volumes and said measured vessel parameters.

2. The method as defined by claim 1, wherein said step of identifying opacified vessels in said images comprises:
   selecting a starting point in an opacified vessel;
   initiating tracking of said selected opacified vessel at said selected starting point;
   measuring said vessel parameters, including local vessel size, for said selected opacified vessel at said selected starting point;
   comparing values of the measured vessel parameters with preset threshold values;
   identifying a next tracking point in said opacified vessel and identifying starting points of branches of said opacified vessels if said measured vessel parameters exceed said preset threshold values;
   repeating said steps of measuring, comparing and identifying if measured vessel parameters exceed the said preset threshold values; and
   terminating tracking of said opacified vessel if said measured vessel parameters do not exceed said preset threshold values.

3. The method according to claim 2, wherein said step of identifying starting points of branches of said opacified vessels comprises:
   determining if one of said starting points of branch vessels has not been employed in said step of initiating tracking if vessel tracking of said opacified vessel has been terminated;
   selecting said one of said starting points of branch vessels as a next starting point of a respective branch vessel to be next tracked if said respective branch vessel has not been previously tracked;
   if said respective branch vessel has not been previously tracked, initiating tracking of said respective branch vessel at said next starting point,
   repeating said steps of measuring, comparing and identifying if said values of said vessel parameters of said respective vessel exceed said preset threshold values, and
   repeating said steps of terminating, determining, and initiating if said values of said vessel information do not exceed said present threshold values; and
   halting tracking if all of said branch vessels have been tracked.

4. The method according to claim 2, wherein the double-square-box region-of-search step comprises:
   centering on one said tracking points a first square box of width equal to twice said vessel size;
   comparing the pixel values of pixels on the perimeter of said first square box to find local maxima on said perimeter;
   identifying the maximum of said local maxima as a prospective next tracking point;
   identifying others of said local maxima as starting points of branches;
   calculating tracking direction as a vector from said one said tracking point to said prospective next tracking point;
   ascertaining the existence of a tracking point immediately previous to said one said tracking point;
   selecting as the next tracking point said prospective next tracking point if said tracking point immediately previous does not exist;
   determining a previous tracking direction as a vector from the tracking point immediately previous to said one said tracking point to said one said tracking point if said tracking point immediately previous does exist;
   comparing said tracking direction with said previous tracking direction if said tracking point immediately previous does exist;
   selecting as a next tracking point said prospective next tracking point if said tracking point immediately previous does exist and change in tracking direction determined in said step of comparing does not exceed a preset threshold value; and
   selecting a next tracking point using a second square box if said tracking point immediately previous does exist and change in tracking direction determined in said step of comparing does exceed a preset threshold value.

5. The method defined by claim 4, wherein said step of determining a next tracking point using a second square box on said tracking point comprises:
   centering on said one of said tracking points a second square box of width equal to the said vessel size;
   comparing the pixel values of pixels on the perimeter of said second square box to find a maximum pixel value on the perimeter of said second square box; and selecting said maximum pixel value on the perimeter of the second square box as the next tracking point.

6. The method defined by claim 1, wherein said vessel parameter measuring step includes a step of measuring the size of the vessel by means of an iterative deconvolution step for vessels with sizes comparable to or less than a width of a line spread function of an imaging system from which said digital X-ray images were obtained.

7. The method defined in claim 6, wherein said iterative deconvolution step comprises:

obtaining actual vessel profiles from pixels lying along lines oriented perpendicular to the vessel axis in said images;

generating ideal vessel profiles by convolution of X-ray patterns of circular vessels with the line spread function of said imaging system;

comparing said ideal and actual vessel profiles using by determining root-mean-square differences therebetween;

changing the vessel size of said circular vessel if said root-mean-square difference is not minimum; and selecting the vessel size of said circular vessel which yields the minimum of said root-mean-square differences to be the true vessel size.

8. The method defined by claim 1, wherein said step of deriving density curves comprises:

interpolating additional density curves from the density curves derived from said images to simulate higher frame rates than that used during acquisition of said images.

9. The method defined by claim 1, wherein the step of correlating said density curves correlates distance-density curves from different images to measure distances traversed by said contrast material as a function of time and comprises:

comparing the difference between a pair of said distance-density curves;

shifting one of said pair of said distance-density curves by selected distances until said difference is minimized;

selecting said distance for which said difference is minimized to be the distance that said contrast material traversed between acquisitions of said pair of images; and representing said selected distance as a function of time.

10. The method defined by claim 1, wherein the step of correlating said density curves produces volume-density curves representing the volume traversed by said contrast material as a function of time and comprises:

comparing the difference between a pair of said distance-density curves;

shifting one of said pair of volume-density curves by selected volumes until said difference is minimized;

selecting said volume for which said difference is minimized to be the volume that said contrast material traversed between acquisitions of said pair of images; and representing said selected volume as a function of time.

11. The method defined by claim 1, wherein the step of correlating measures distances traversed by said contrast material as a function of time, and said step of calculating comprises:

obtaining cumulative-distance curves as a function of time by summing said distance traversed by the contrast medium from the first image onward as a function of time;

calculating instantaneous velocities from the slopes of said cumulative-distance curves;

calculating the average cross-sectional area of said vessel from said vessel parameters;

calculating instantaneous flow rates by multiplying said instantaneous velocities by said average cross-sectional area of said vessel;

calculating average velocities from the slopes of lines fitted to the said cumulative-distance curves; and calculating average flow rates by multiplying said average velocities by said average cross-sectional area of said vessel.

12. The method defined by claim 1, wherein the step of correlating measures volumes traversed by said contrast material as a function of time, and said step of calculating comprises:

obtaining cumulative-volume curves as a function of time by summing said volume traversed from the first image onward as a function of time;

calculating instantaneous flow rates from the slopes of said cumulative-volume curves;

calculating the average cross-sectional area of said vessel from said vessel parameters;

calculating instantaneous flow velocities by dividing said instantaneous flow rates by said average cross-sectional area of said vessel;

calculating average flow rates from the slopes of lines fitted to said cumulative-volume curves; and calculating average flow velocities by dividing said average flow rates by said average cross-sectional area of said vessel.

13. A system for automated measurement of instantaneous and average blood flow rates using a digital X-ray image, comprising the steps of:

means for generating a sequence of digital X-ray images of an object as a contrast material is injected into the object;

means for storing said images;

means for identifying opacified vessels in each of said images;

means for measuring selected vessel parameters, including vessel size, contrast, and position, of the opacified vessels identified in said identifying means;

means for identifying the same vessel in different of said images;

means for deriving vessel longitudinal density curves representing vessel contrast as a function of one of longitudinal distance or volume along the length of said vessel based on the measured vessel contrast;

means for correlating said density curves from different images to measure one of distances or volumes traversed by said contrast material as a function of time; and means for calculating at least one of instantaneous and average flow velocities and flow rates in said vessels from the measured one of distances or volumes and said measured vessel parameters.

14. The system as defined by claim 13, wherein said means for identifying opacified vessels in said images comprises:

means for selecting a starting point in an opacified vessel;

means for initiating tracking of said selected opacified vessel at said selected starting point;

means for measuring said vessel parameters, including local vessel size, for said selected opacified vessel at said selected starting point;

means for comparing values of the measured vessel parameters with preset threshold values;

means for identifying a next tracking point in said opacified vessel and identifying starting points of branches of said opacified vessels if said measured vessel parameters exceed said preset threshold values;

means for repeating said steps of measuring, comparing and identifying if said measured vessel parameters exceed said present threshold values; and means for terminating tracking of said opacified vessel if said measured vessel parameters do not exceed said present threshold values.

15. The system according to claim 14, wherein said vessel tracking means further comprises:

means for determining if one of said starting points of branch vessels has not been employed in said step of initiating tracking if vessel tracking of said opacified vessel has been terminated;

means for selecting said one of said starting points of branch vessels as a next starting point of a respective branch vessel to be next tracked if said respective branch vessel has not been previously tracked;

means, if said respective branch vessel has not been previously tracked, for performing the functions of, initiating tracking of said respective branch vessel at said next starting point, repeating measuring, comparing and identifying if said values of said vessel parameters of said respective vessel exceed said preset threshold values, and repeating terminating, determining, and initiating if said values of said vessel information do not exceed said preset threshold values; and means for halting tracking if all of said branch vessels have been tracked.

16. The system as defined by claim 14, wherein the means for identifying a next tracking point further comprises:

means for centering on one said tracking points a first square box of width equal to twice said vessel size;

means for comparing the pixel values of pixels on the perimeter of said first square box to find local maxima on said perimeter;

means for identifying the maximum of said local maxima as a prospective next tracking point;

means for identifying others of said local maxima as starting points of branches;

means for calculating tracking direction as a vector from said one said tracking point to said prospective next tracking point;

means for ascertaining the existence of a tracking point immediately previous to said one said tracking point;

means for selecting as the next tracking point said prospective next tracking point if said tracking point immediately previous does not exist;

means for determining a previous tracking direction as a vector from the tracking point immediately previous to said one said tracking point to said one said tracking point if said tracking point immediately previous does exist;

means for comparing said tracking direction with said previous tracking direction if said tracking point immediately previous does exist;

means for selecting as a next tracking point said prospective next tracking point if said tracking point immediately previous does exist and change in tracking direction determined by said means for comparing does not exceed a preset threshold value; and means for selecting a next tracking point using a second square box if said tracking point immediately previous does exist and change in tracking direction determined by said means for comparing does exceed a preset threshold value.

17. The system defined by claim 16, wherein said means for determining a next tracking point rising a second square box comprises:

means for centering on said one of said tracking points a second square box of width equal to said vessel size;

means for comparing the pixel values of pixels on the perimeter of said second square box to find a maximum pixel value on the perimeter of said second square box; and means for selecting said maximum pixel value on the perimeter of the second square box as the next tracking point.

18. A system defined by claim 13, wherein said vessel parameter measuring means comprises:

means for measuring the size of the vessel by means of an iterative deconvolution for vessels with sizes comparable to or less than a width of a line spread function of said image generating means.

19. The system defined in claim 18, wherein said means for measuring by means of said iterative deconvolution step comprises:

means for obtaining actual vessel profiles from pixels lying along lines oriented perpendicular to the vessel axis in said images;

means for generating ideal vessel profiles by convolution of X-ray patterns of circular vessels with the line spread function of the image generating means;

means for comparing said ideal and actual vessel profiles by determining root-mean-square differences therebetween;

means for changing the vessel size of said circular vessel if said root-means-square difference is not a minimum; and means for selecting the vessel size of the circular vessel which yields the minimum of said root-mean-square differences to be the true vessel size.

20. The system defined by claim 13, wherein said means for deriving density curves comprises:

means for interpolating additional density curves from the density curves derived from said images to simulate higher frame rates than that used during acquisition of said images.

21. The system defined by claim 13, wherein said means for correlating said density curves correlates distance-density curves to measure distances traversed by said contrast material as a function of time and comprises:

means for comparing the difference between a pair of said distance-density curves;

means for shifting one of said pair of said distance-density curves by selected distances until said difference is minimized;

means for selecting the distance for which said difference is minimized to be the distance that said contrast material traversed between acquisitions of said pair of images; and means for representing said selected distance as a function of time.

22. The system defined by claim 13, wherein said means for correlating said density curves produces volume-density curves representing the volume traversed by said contrast material as a function of time and comprises:

means for comparing the difference between a pair of said volume-density curves;

means for shifting one of said pair of volume-density curves by selected volumes until said difference is minimized;

means for selecting the volume for which said difference is minimized to be the volume that said contrast material traversed between acquisitions of said pair of images; and means for representing said selected volume as a function of time.

23. The system defined by claim 13, wherein said means for correlating measures distances traversed by said contrast material as a function of time, and said means for calculating comprises:

means for obtaining cumulative-distance curves as a function of time by summing the distance traversed by the contrast medium from the first image onward as a function of time;

means for calculating instantaneous velocities from the slopes of said cumulative-distance curves;

means for calculating the average cross-sectional area of said vessel from said vessel parameters;

means for calculating instantaneous flow rates by multiplying said instantaneous velocities by said average cross-sectional area of said vessel;

means for calculating average velocities from the slopes of lines fitted to the cumulative-distance curves; and means for calculating average flow rates by multiplying said average velocities by said average cross-sectional area of said vessel.

24. The system defined by claim 13, wherein said means for correlating measures volumes traversed by said contrast material as a function of time, and said means for calculating comprises:

means for obtaining cumulative-volume curves as a function of time by summing volume traversed from the first image onward as a function of time;

means for calculating instantaneous flow rates from the slopes of said cumulative-volume curves;

means for calculating the average cross-sectional area of said vessel from said vessel parameters;

means for calculating instantaneous flow velocities by dividing said instantaneous flow rates by said average cross-sectional area of said vessel;

means for calculating average flow rates from the slopes of lines fitted to said cumulative-volume curves; and means for calculating average flow velocities by dividing said average flow rates by said average cross-sectional area of said vessel.

* * * * *